United States Patent [19]
Siegall et al.

[11] Patent Number: 5,597,569
[45] Date of Patent: Jan. 28, 1997

[54] **BRYODIN 2 A RIBOSOME-INACTIVATING PROTEIN ISOLATED FROM THE PLANT *BRYONIA DIOICA***

[75] Inventors: Clay B. Siegall, Edmonds; Susan L. Gawlak, Bellevue; Hans Marquardt, Mercer Island, all of Wash.

[73] Assignee: Bristol-Myers Squibb Company, New York, N.Y.

[21] Appl. No.: 324,301

[22] Filed: Oct. 20, 1994

Related U.S. Application Data

[63] Continuation-in-part of Ser. No. 141,891, Oct. 25, 1993, abandoned.

[51] Int. Cl.$^6$ .................... A61K 39/44; C07K 14/415; C07K 16/46
[52] U.S. Cl. .................... 424/183.1; 424/178.1; 530/300; 530/350; 530/370; 530/391.7; 536/23.1; 536/23.4; 536/23.5; 536/23.6; 514/2; 514/8; 435/69.1; 435/69.7; 435/71.1; 435/172.4; 435/171.3; 435/320.1
[58] Field of Search .................... 424/178.1, 179.1, 424/183.1; 530/391.7, 391.9, 391.5, 403, 300, 350, 370, 810, 812, 395, 402; 536/23.1, 23.4, 23.5, 23.6; 514/2, 8; 435/69.1, 69.7, 71.1, 172.1, 172.3, 320.1

[56] References Cited

U.S. PATENT DOCUMENTS 5,242,813  9/1993  Pastan .................... 435/70.21

FOREIGN PATENT DOCUMENTS 0290040   3/1990  European Pat. Off. ........ C07K 15/14
2194948   8/1987  United Kingdom ........... C07K 15/00
WO91/00295 1/1991  WIPO ............................. C07K 15/28

OTHER PUBLICATIONS

Goldenberg Ca Cancer J Clin:44:43–64(1994).
Siegal et al. Bioconjugate Chem. 5:423–429(1994).
C. Z. Amorim et al., "Screening of the Antimalarial Activity of Plants of the Cucurbitaceae Family," *Mem. Inst. Oswaldo Cruz* 86:177–180, 1991.

Y. Endo et al., "RNA N–Glycosidase Activity of Ricin A–chain," *J. Biol. Chem.* 262:8128–8130, 1987.

P.–C. Montecucchi et al., "N–terminal sequence of some ribosome–inactivating proteins," *Int. J. Peptide Protein Res.* 33:263–267, 1989.

T. B. Ng et al., "Proteins with abortifacient, ribosome inactivating, immunomodulatory, antitumor and anti–AIDS activities from Cucurbitaceae plants," *Gen. Pharmac.* 23:575–590, 1992.

F. Stirpe et al., "Bryodin, a ribosome–inactivating protein from the roots of *Bryomia dioica* L. (white bryony),," *Biochem. J.* 240:659–665, 1986.

F. Stirpe et al., "Modification of ribosomal RNA by ribosome–inactivating proteins from plants," *Nucleic Acids Research* 16:1349–1357, 1988.

P. N. Friedman et al., "Antitumor Activity of the Single–Chain Immunotoxin BR96 sFv–PE40 against Established Breast and Lung Tumor Xenografts," *J. Immunol.* 150:3054–3061, 1993.

C. B. Siegall et al., "Characterization of Ribosome–Inactivating Proteins Isolated from *Bryonia dioica* and Their Utility as Carcinoma–Reactive Immunoconjugates," *Bioconjugate Chem.* 5:423–429, 1994.

*Primary Examiner*—Christina Y. Chan
*Assistant Examiner*—Phillip Gambel

[57] ABSTRACT

The present invention discloses a new ribosome-inactivating protein, bryodin 2, isolated from the plant *Bryonia dioica*. This ribosome-inactivating protein (RIP) is a type I RIP having a single polypeptide chain and no cellular receptor domain. Like many type I RIPs, bryodin 2 has a molecular weight of about 27,000 daltons and a pI of 9.5. Bryodin 2 differs from previously identified ribosome-inactivating protein in its amino acid composition, amino acid sequence, and toxicity in vitro and in vivo. Bryodin 2 is useful, as are other type I ribosome-inactivating proteins, as an abortifacient, immunomodulator, anti-tumor or anti-viral agent. Compositions comprising bryodin 2 as an immunoconjugate or fusion molecule are particularly useful to kill cells of a target population.

41 Claims, 16 Drawing Sheets

```
BD2       VDINFSLIGATGATYKTFIRNLRTTLTVGTPR
BD1          DVSFRLSGATTTSYGVFIKNLREALPYERKV
RA        IFPKQYPIINFTTAGATVQSYTNFIRAVRGRLTTGADV
α-MMC        DVSFRLSGADPRSYGMFIKDLRNALPFREKV
TCS          DVSFRLSGATSSSYGVFISNLRKALPNERKL
Luffin A     DVRFSLSGSSSTSYSKFIGDLRKALPSNGTV
```

Figure 5

| PEPTIDE | SEQUENCE |
|---|---|
| | 1          10          20          30          40 |
| N Term | VDINFSLIGATGATYKTFIRNLRTTLTVGTPR |
| T10 | LPYGGNYDGLETAAGR |
| T21 | ENIELGFSEISSAIGNMFR |
| M4 | FRHNPGTSVPRAFIVIIQTVSEAARFKYIEQR |
| M4/K2 | YIEQRVSENVGTK |
| M4/K11 | FKPDPAFLSLQNAWGSLSEQIQIAQTRGGEFARPVELRT |
| M4/E4 | LRTVSNTPTFVTNVN |

Figure 6

```
BD2                     VDINFSLIGATGATYKTFIRNLRTTLTVGTPR
MOM  MVKCLLLSFLIIAIFIGVPTAKGDVNFDLSTATAKTYTKFIEDFRATLPFSHKV    54

BD2
MOM  YDIPLLYSTISDSRRFILLDLTSYAYETISVAIDVTNVYVVAYRTRDVSYFFKES   109

BD2                  LPYGGNYDGLETAAGR--ENIELGFSEISSAIGNMFRHN
MOM  PPEAYNILFKGTRKITLPYTGNYENLQTAAHKIRENIDLGLPALSSAITTLFYYN   164

BD2  PGTSVPRAFIVIIQTVSEAARFKYIEQRVSENVGTKFKPDPAFLSLQNAWGSLSE
MOM  -AQSAPSALLVLIQTTAEAARFKYIERHVAKYVATNFKPNLAIISLENQWSALSK   218

BD2  QIQIAQTRGGEFARPVELRTVSNTPTFVTNVN
MOM  QIFLAQNQGGKFRNPVDLIKPTGERFQVTNVDSDVVKGNIKLLLNSRASTADENF   273

BD2
MOM  ITTMTLLGESVVN                                             286
```

Figure 7

```
GGGGGCCAAATTGGAAGGAAAATAAAT ATG AGA TCG ATT GGG TTT TAC TCT GTT  54
                            M   R   S   I   G   F   Y   S   V    9
                                            1
CTA GCT CTG TAT GTT GGT GCT CAT GTT ACA GAG GAC GTT GAT ATC AAC 102
 L   A   L   Y   V   G   A   H   V   T   E   D   V   D   I   N   25
                     10                                  20
TTC TCT CTA ATA GGT GCG ACT GGT GCA ACC TAC AAA ACT TTT ATA AGG 150
 F   S   L   I   G   A   T   G   A   T   Y   K   T   F   I   R   41
                             30
AAT CTG CGC ACC AAA CTC AGC GTT GGA ACT CCA AGG GTG TAC GAT ATA 198
 N   L   R   T   K   L   S   V   G   T   P   R   V   Y   D   I   57
             40                              50
CCT GTC CTG AGA AAC GCA GCA GCC GGG CTC GCG CGC TTT CAA TTA GTT 246
 P   V   L   R   N   A   A   A   G   L   A   R   F   Q   L   V   73
                             60
ACC CTC ACA AAT TAC AAT GGC GAA TCT GTC ACT GTG GCT TTA GAT GTA 294
 T   L   T   N   Y   N   G   E   S   V   T   V   A   L   D   V   89
     70                                              80
GTG AAC GTG TAC GTT GTT GCA TAT CGA GCT GGA AAC ACT GCT TAC TTT 342
 V   N   V   Y   V   V   A   Y   R   A   G   N   T   A   Y   F  105
                     90                                  100
CTC GCA GAT GCA TCA ACA GAA GCC AAC AAT GTG TTG TTT GCA GGC ATC 390
 L   A   D   A   S   T   E   A   N   N   V   L   F   A   G   I  121
                                     110
AAT CAT GTA AGA CTT CCT TAT GGA GGG AAT TAC GAT GGC CTT GAG ACA 438
 N   H   V   R   L   P   Y   G   G   N   Y   D   G   L   E   T  137
             120                                 130
GCT GCA GGC AGA ATT TCG AGG GAA AAT ATT GAA CTT GGA TTT TCC GAA 486
 A   A   G   R   I   S   R   E   N   I   E   L   G   F   S   E  153
                             140
ATA AGT AGT GCC ATT GGC AAC ATG TTC CGC CAC AAC CCT GGT ACG TCT 534
 I   S   S   A   I   G   N   M   F   R   H   N   P   G   T   S  169
     150                                 160
GTC CCT AGA GCA TTT ATT GTC ATC ATC CAA ACA GTC TCT GAG GCT GCG 582
 V   P   R   A   F   I   V   I   I   Q   T   V   S   E   A   A  185
                     170                                 180
AGA TTT AAA TAT ATC GAG CAA AGA GTT TCT GAA AAT GTT GGA ACA AAG 630
 R   F   K   Y   I   E   Q   R   V   S   E   N   V   G   T   K  201
                             190
TTT AAG CCA GAC CCT GCG TTT TTG AGC TTG CAA AAT GCT TGG GGC AGT 678
 F   K   P   D   P   A   F   L   S   L   Q   N   A   W   G   S  217
             200                                 210
CTC TCT GAA CAA ATA CAA ATC GCA CAA ACT CGC GGA GGG GAA TTT GCT 726
 L   S   E   Q   I   Q   I   A   Q   T   R   G   G   E   F   A  233
                             220
CGT CCT GTC GAG CTT CGA ACT GTT AGC AAC ACT CCG ACT TTT GTG ACC 774
 R   P   V   E   L   R   T   V   S   N   T   P   T   F   V   T  249
     230                                 240
AAT GTT AAT TCG CCT GTT GTG AAA GGC ATT GCA CTT CTA CTG TAC TTT 822
 N   V   N   S   P   V   V   K   G   I   A   L   L   L   Y   F  265
                     250                                 260
AGA GTT AAT GTT GGC ACT GAT AAT GTT TTC GCA ATG TCC TTG TCA ACC 870
 R   V   N   V   G   T   D   N   V   F   A   M   S   L   S   T  281

TAC TAG TAC TCA TCA ATC AAA CTA TAC TGT GTG CTT GTA TGT GCA AGT 918
 Y   *   stop                                                   282

ATG GCA ATA ATA AAG ACT TAA TCC TTT ATG TTA AAA AAA AAA AA      963
```

Figure 12

| | | |
|---|---|---|
| BD2 | MRSIGFYSVLALYVGAHV-TEDVDINFSLIGATGATYKTFIRNLRTTLTVGTPR | 53 |
| MOM | MVKCLLLSFLIIAIFIGVPTAKGDVNFDLSTATAKTYTKFIEDFRATLPFSHKV | 54 |
| | | |
| BD2 | VYDIPVLRNAAAGLARFQLVTLTNYNGESVTVALDVVNVYVVAYRAGNTAYFLAD | 108 |
| MOM | -YDIPLLYSTISDSRRFILLDLTSYAYETISVAIDVTNVYVVAYRTRDVSYFFKE | 108 |
| | | |
| BD2 | ASTEANNVLFAGINHVRLPYGGNYDGLETAAG--RENIELGFSEISSAIGNMFRHN | 162 |
| MOM | SPPEAYNILFKGTRKITLPYTGNYENLQTAAHKIRENIDLGLPALSSAITTLFYYN | 164 |
| | | |
| BD2 | PGTSVPRAFIVIIQTVSEAARFKYIEQRVSENVGTKFKPDPAFLSLQNAWGSLSE | 217 |
| MOM | -AQSAPSALLVLIQTTAEAARFKYIERHVAKYVATNFKPNLAIISLENQWSALSK | 218 |
| | | |
| BD2 | QIQIAQTRGGEFARPVELRTVSNTPTFVTNVNSPVVKG-IALLLYFRVNVGTDNV | 271 |
| MOM | QIFLAQNQGGKFRNPVDLIKPTGERFQVTNVDSDVVKGNIKLLLNSRASTADENF | 272 |
| | | |
| BD2 | FA-MSLSTY | 279 |
| MOM | ITTMTLLGESVVN | 286 |

Figure 13

BRYODIN 2 A RIBOSOME-INACTIVATING PROTEIN ISOLATED FROM THE PLANT *BRYONIA DIOICA*

CROSS REFERENCE

This application is a continuation-in-part of U.S. patent application Ser. No. 08/141,891, now abandoned, filed Oct. 25, 1993, the content thereof is hereby incorporated by reference in its entirety.

FIELD OF THE INVENTION

The present invention relates to the isolation and characterization of a novel ribosome-inactivating protein from the plant *Bryonia dioica*. The oligonucleotide sequence encoding the protein and its amino acid sequence have been determined. The invention also relates to immunoconjugates comprising the new protein and antibodies immunologically specific for various tumor-associated antigens and to recombinantly constructed fusion proteins having ribosome-inactivating activity and the ability to target specific cells. Methods for the recombinant expression and chemical synthesis of this protein are considered part of the present invention. Use of these immunoconjugates and toxin fusion proteins in the treatment of cancer and as an active agent of various pharmacologic compositions is also considered part of the present invention.

BACKGROUND OF THE INVENTION

Proteins which inhibit protein synthesis have been isolated from various organisms including plants, bacteria and fungi. These protein toxins are thought to be produced by the organisms in order to provide a selective advantage for the growth of the organisms that produce them. Despite the divergent evolutionary background of the organisms in which these protein toxins are found, most toxins have strikingly similar mechanisms of action. One particular group of toxins exerts its action by blocking protein synthesis either by directly modifying elongation factor 2 (EF-2) or by modifying the ribosome itself so that EF-2 cannot function in protein synthesis. This class of toxins, ribosome-inactivating proteins (RIPs), can be isolated from plants of several families.

Plant ribosome-inactivating proteins have been divided into two groups based on their structure. Type I ribosome-inactivating proteins (type I RIPs) contain a single chain that has ribosome-inactivating activity. Examples of type I RIPs include gelonin, saporin, trichosanthin and bryodin. Type II ribosome-inactivating proteins (type II RIPs) are comprised of two chains, an A chain that is able to inactivate EF-2, and a B chain, that contains a cell binding domain having lectin-like properties. The binding domain enables type II RIPs to bind many cell types and to kill those cells. Examples of type II RIPs are ricin and abrin.

Although the two types of ribosome-inactivating proteins differ in their structures, both types inhibit protein synthesis by inactivating the 60S subunit of eukaryotic ribosomes through cleavage of the N-glycosidic bond of the adenine residue at position 4324 of 28 S rRNA (Endo and Tsurugi 1987, *J. Biol. Chem.* 262:8128–8130; Stirpe, F. et al. 1988, *Nucl. Acid Res.*, 16:1349–1357).

Ribosome-inactivating proteins have been isolated from several families of plants including the Cariophyllaceae, Cucurbitaceae, Euphorbiaceae and Phytolaccaceae. The toxins have been isolated particularly from the root, seeds and leaves of the plants. Comparisons have been made of the N-terminal amino acid sequences of RIPs isolated from the seeds of *Gelonium multifiorum* (Euphorbiaceae), *Momordica charantia* (Cucurbitaceae), *Bryonia dioica* (Cucurbitaceae), *Saponaria officinalis* (saporin-5a, saporin-5b, saporin-6a, saporin-6b) (Cariophyllaceae) and from the leaves of *Saponaria officinalis* (saporin-1). Complete amino acid sequences have been determined for a Type I RIP from *Trichosanthes kirilowii* maxim and from Barley seed protein synthesis inhibitor. These comparisons show that at least the N-terminal regions of the toxins bryodin and momordin (members of the Curcurbitaceae family) show a high level of similarity with ricin A chain and with gelonin which are members of the Euphorbiaceae family. The similarity is thought to be a consequence of a similar evolutionary origin. Very little similarity was found between RIPs of the Cucurbitaceae and Euphorbiaceae families and those of the Phytolaccaceae or Cariophyllaceae families (Montecucchi et al., 1989, *Int. J. Peptide Protein Res.* 33:263–267). Although similarities are found in the amino acid sequences of the N-terminal regions of RIPs isolated from the same species, many differences do exist particularly between toxins isolated from different tissue of the same plant.

A plant protein toxin designated bryodin was initially identified as a 27–30 kDal protein isolated from the root of *Bryonia dioica* (United Kingdom Patent Application GB2194948, published Mar. 23, 1988). The toxin is a type I ribosome-inactivating protein having a single chain and a mechanism of action, which inactivates ribosomes by blocking productive interactions with elongation factor-2. In not having a cell binding domain, bryodin, like the other type I RIPs, does not normally bind to mammalian cells. The protein has been shown to have a molecular weight by gel filtration of about 27,300 daltons and about 28,800 daltons by polyacrylamide gel electrophoresis, and an isoelectric point of 9.5. This toxin was found to inhibit protein synthesis in the rabbit reticulocyte lysate system with wheat germ ribosomes at 3.6 ng/ml ($ID_{50}$) and an $LD_{50}$ in mice of 14.5 mg/kg when administered intraperitoneally. The N-terminal amino acid sequence has been determined to be

```
              5                    10                   15
Asp—Val—Ser—Phe—Arg—Leu—Ser—Gly—Ala—Thr—Thr—Thr—Ser—Tyr—Gly—Val—

20                   25                   30
Phe—Ile—Lys—Asn—Leu—Arg—Glu—Ala—Leu—Pro—Tyr—Glu—Arg—Lys—Val—Tyr—

35                   40
Asn—Ile—Pro—Leu—Leu—Leu—Arg—His—Xxxx—Ile—Gly—    (SEQ ID NO:8)
``` of two chains, an A chain that is able to inactivate EF-2, and a B chain, that contains a cell binding domain having lectin-like properties. The binding domain enables type II RIPs to bind many cell types and to kill those cells. Examples of type II RIPs are ricin and abrin.

A second ribosome-inactivating protein has been isolated from the leaves of *B. dioica* (European Patent Publication EPO 390 040, published Oct. 3, 1990). This molecule has been described as having a molecular weight of 27,300 daltons by gel filtration and 28,800 daltons by polyacrylamide gel electrophoresis, and an isoelectric point of 9.5 and has been designated bryodin-L. This form of bryodin was found to inhibit protein synthesis in a rabbit reticulocyte lysate system with an $EC_{50}$ of 0.1 nM (3.6 ng/ml) and has an $LD_{50}$ in mice of 10 mg/kg when administered intraperitoneally. An amino acid analysis was also provided, but no amino acid sequence has been disclosed.

Ribosome-inactivating proteins are of interest because of their usefulness as components of "immunotoxins." Immunotoxins are hybrid molecules consisting of a toxic moiety linked to an antibody capable of selectively directing the toxin to a specific target cell. Potential target cells include harmful cells, i.e., neoplastic, virally infected, immunocompetent or parasitic cells. Immunotoxins as defined in the present invention can be chemical conjugates of a cell-specific ligand linked to a toxic molecule, such as a ribosome-inactivating protein. The fact that many different ribosome-inactivating proteins are known and that new toxins are being discovered provides a variety of toxic moieties which have varying levels of intrinsic toxicity on whole cells when unconjugated and provide an available source of alternative toxins should the patient develop an immune response during long term in vivo treatment to the originally administered immunotoxin. In addition, some immunotoxins, saporin 6 and an anti-Thy 1.1 antibody or its $F(ab')_2$ fragment, were more toxic than free toxin providing a need for new and different toxin molecules.

The present invention provides a novel plant protein toxin isolated from *Bryonia dioica* we have designated bryodin 2, which is distinguishable from bryodin and bryodin-L by its oligonucleotide sequence, amino acid sequence, amino acid composition, toxicity in animals and immunogenicity. Bryodin 2 provides a new ribosome-inactivating protein that can be used to form additional and possibly better immunotoxins and toxin fusion molecules for use in formulating pharmaceutical compositions for use in treating cancer, certain viral infections, modulating the immune response, and other diseases.

SUMMARY OF THE INVENTION

The present invention comprises a novel ribosome-inactivating protein comprising a single-chain protein having a molecular weight of about 27,000 daltons by polyacrylamide gel electrophoresis under reducing and non-reducing conditions, an $EC_{50}$ of about 0.017 mM in a rabbit reticulocyte lysate system, an $LD_{50}$ in mice of greater than 10 mg/kg when administered intravenously and about 8 mg/kg when administered intraperitoneally. The ribosome inactivating protein of the invention further comprises an amino acid composition determined on a residue per mole basis comprising:

| Lys | 0.4 | Ala | 28.7 |
|---|---|---|---|
| His | Below detection | 1/2 Cys | Below detection |
| Arg | 8.5 | Val | 34.2 |
| Asx | 14.0 | Met | Below detection |
| Thr | 13.1 | Ile | 23.3 |
| Ser | 6.5 | Leu | 28.3 |
| Glx | 38.2 | Tyr | 5.0 |
| Pro | 15.0 | Phe | 18.5 |
| Gly | 11.1 | Trp | Not determined |

This novel ribosome-inactivating protein was isolated from the plant *Bryonia dioica*, and has been designated bryodin 2. Bryodin 2 differs from ribosome-inactivating proteins previously isolated from *B. dioica* and other plants in its nucleotide and amino acid sequence, and in its amino acid composition, protein synthesis inhibitory activity and immunoreactivity in various biological assays.

A second embodiment of the present invention comprises an isolated oligonucleotide sequence which encodes the ribosome-inactivating protein isolated from *Bryonia dioica* having the amino acid sequence of bryodin 2 as depicted in SEQ ID NO: 15, or a complement of the isolated oligonucleotide. In particular the isolated oligonucleotide sequence can comprise the oligonucleotide sequence depicted in SEQ ID NO: 14 or a fragment thereof which encodes a protein capable of inactivating a ribosome and preventing protein synthesis.

In another embodiment of the present invention, the ribosome-inactivating protein comprises an N-terminal amino acid sequence comprising the following contiguous amino acid sequence:

```
   1              5                  10
Val Asp Ile Asn Phe Ser Leu Ile Gly Ala
              15                 20
Thr Gly Ala Thr Tyr Lys Thr Phe Ile Arg
              25                 30
Asn Leu Arg Thr Thr Leu Thr Val Gly Thr

Pro Arg (SEQ ID NO:1).
```

The ribosome-inactivating protein can also further be comprised of a contiguous internal amino acid residue sequence of:

```
  105           110                         (a)
Leu Pro Tyr Gly Gly Asn Tyr Asp Gly Leu
  115           120
Glu Thr Ala Ala Gly Arg (SEQ ID NO:2);

125            130                   (b)
Glu Asn Ile Glu Leu Gly Phe Ser Glu Ile
     135            140
Ser Ser Ala Ile Gly Asn Met Phe Arg (SEQ ID NO:3);

145             150           (c)
Phe Arg His Asn Pro Gly Thr Ser Val Pro
            155             160
Arg Ala Phe Ile Val Ile Ile Gln Thr Val
            165             170
Ser Glu Ala Ala Arg Phe Lys Tyr Ile Glu

Gln Arg (SEQ ID NO:4);

170             175                  (d)
Tyr Ile Glu Gln Arg Val Ser Glu Asn Val
     180
Gly Thr Lys (SEQ ID NO:5);

185             190           (e)
Phe Lys Pro Asp Pro Ala Phe Leu Ser Leu
            195             200
Gln Asn Ala Trp Gly Ser Leu Ser Glu Gln
            205             210
Ile Gln Ile Ala Gln Thr Arg Gly Gly Glu
              215
Phe Ala Arg Pro Val Glu Leu Arg Thr (SEQ ID NO:6);

or 220             225              (f)
Leu Arg Thr Val Ser Asn Thr Pro Thr Phe
     230
Val Thr Asn Val Asn (SEQ ID NO:7).
```

In yet another embodiment of the present invention, methods for the recombinant expression of the ribosome-inactivating protein of the present invention are described. The recombinantly produced protein can be bryodin 2, fragments or derivatives of bryodin 2 having ribosome-inactivating activity. The methods comprise preparing complementary or genomic DNA which encodes bryodin 2, fragments or derivatives thereof, constructing a vector comprising the coding sequence operatively linked with transcriptional and translational elements necessary for expression in a host cell, transforming the host cell with the expression vector, incubating the transformed host cell under conditions conducive to expression of the inserted coding sequence, and isolating the expressed ribosome inactivating protein.

In a further embodiment, the ribosome-inactivating protein of the present invention can be used to form an immunotoxin or toxin-ligand conjugate. The immunotoxin comprises a ligand or molecule that specifically binds or reactively associates or complexes with a receptor or other receptive moiety associated with a target cell population linked to the toxin. Ligands of the invention can be an immunoglobulin, adhesion molecule, or a polypeptide, peptide or non-peptide molecule. Preferably, the ligand can be, but is not limited to, transferrin, an epidermal growth factor, bombesin, gastrin, gastrin-releasing peptide, platelet-derived growth factor, interleukin-2, interleukin-6, a transforming growth factor, steroid, carbohydrate or a lectin. Immunoglobulin molecules specifically immunoreactive with a tumor-associated antigen are particularly preferred. The immunoglobulin can be an antigen recognizing fragment of an intact immunoglobulin, a chimeric antibody, or a hybrid antibody. Immunoglobulins specific for Lewis-Y related antigens which are internalized by tumor cells are of particular interest in the present invention. Specifically, a preferred embodiment of the present invention comprises the chimeric BR96 immunoglobulin as produced by the hybridoma deposited with the American Type Culture Collection 12301 Parklawn Drive, Rockville Md. 20852 on May 23, 1990 and designated ATCC HB10460.

In another embodiment of the present invention, the toxin and/or toxin-ligand conjugate of the present invention can be formulated to form a pharmaceutical composition. Pharmaceutical compositions of the present invention preferably comprise bryodin 2 or bryodin 2-ligand conjugates and a physiologically acceptable or pharmaceutical carrier. Such compositions can also include various buffers, excipients, additives and other molecules to stabilize the pharmaceutical composition.

In yet another embodiment, the ribosome-inactivating protein of the present invention can be used in methods for killing a target cell. Such a method comprises contacting the target cell with an effective amount of a toxin-ligand conjugate comprising the ribosome-inactivating protein and a ligand specific for the target cell. The toxin-ligand conjugate is contacted with the target cell for a time sufficient to kill the target cell. In a preferred embodiment, the toxin-ligand conjugates comprise bryodin 2 and the immunoglobulin chimeric BR96, which, when contacted with tumor cells expressing the BR96 antigen, kills the tumor cells.

In still yet another embodiment, the ribosome-inactivating protein of the present invention is used in a method for inhibiting the proliferation of mammalian tumor cells. The method comprises the steps of contacting the mammalian tumor cells with a composition comprising the ribosome-inactivating protein of the present invention conjugated with a ligand specific for a tumor-associated antigen at a proliferation-inhibiting concentration for a time sufficient to inhibit the proliferation of the mammalian tumor cells. As above, in a most preferred embodiment, the composition comprises bryodin 2 and the immunoglobulin chimeric BR96.

BRIEF DESCRIPTION OF THE DRAWINGS

FIG. 5 is a comparison of the similarity between the N-terminal amino acid sequence of bryodin 2 and other plant toxins. Bryodin 2 (BD2); bryodin 1 (BD 1; SEQ ID NO: 8); ricin A chain (RA; SEQ ID NO: 9); α-momorcharin (αMMC; SEQ ID NO: 10); trichosanthin (TCS SEQ ID NO: 11) and luffin A (SEQ ID NO: 12).

FIG. 6 provides the amino acid sequences obtained for various fragments of the 27,000 protein band isolated from the roots of *Bryonia dioica*, after treatment with cyanogen bromide and certain proteases. N Term. (SEQ ID NO: 1); T10 (SEQ ID NO: 2); T21 (SEQ ID NO: 3), M4 (SEQ ID NO: 4); M/4K2 (SEQ ID NO: 5); Mr/K11 (SEQ ID NO: 6); M4/E4 (SEQ ID NO: 7).

FIG. 7 illustrates the alignment of amino acid sequences obtained from peptide fragments of bryodin 2 with the plant toxin momordin SEQ ID NO: 13).

FIG. 9A is the chromatography profile from the gel filtration column of chiBR96-BD2 conjugate. Fractions 45–55 are the conjugate and unreacted antibody; fractions 64–74 are unreacted antibody. FIG. 9B is the NaCl elution profile of chiBR96-BD2 from Blue-SEPHAROSE (0.4 M NaCl, fraction 1; 0.8M NaCl, fractions 2–8). FIG. 9C is the Coomassie Blue stained SDS-PAGE analysis of fractions of the Blue-SEPHAROSE eluted material (4–12% non-reducing polyacrylamide gel). Lanes 1–4 correspond to fractions 1–4 from panel B, Lane 5=unconjugated chiBR96.

FIG. 12 provides the oligonucleotide sequence encoding bryodin 2 (SEQ ID NO: 14) and the putative amino acid sequence encoded by the oligonucleotide sequence (SEQ ID NO: 15. The oligonucleotide sequence provides for the translation of a mature protein of about 261 amino acid residues with a 21 amino acid residue signal sequence.

FIG. 13 illustrates an alignment of the amino acid sequence obtained for bryodin 2 with the plant toxin momordin.

DETAILED DESCRIPTION OF THE SPECIFIC EMBODIMENTS

Figure 1:
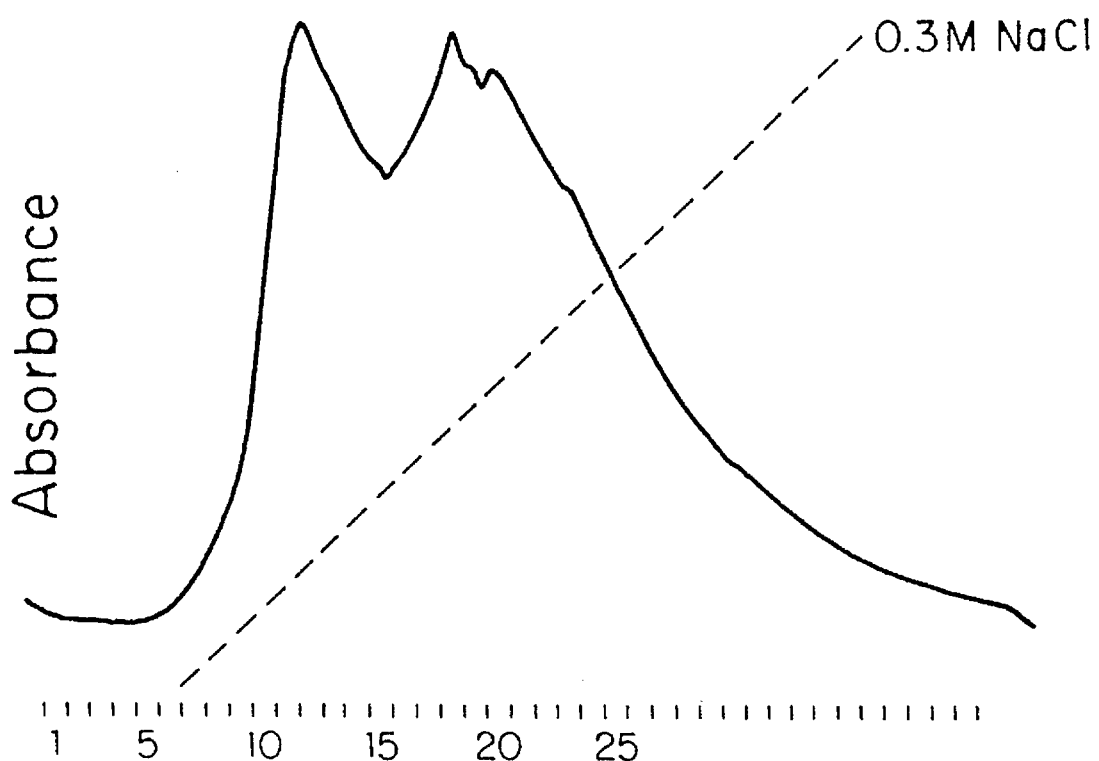
FIG. 1 provides results of the absorbence reading from CM-Sepharose chromatography of protein isolated from the root of *Bryonia dioica*.

The present invention relates to a novel ribosome-inactivating protein toxin isolated from *Bryonia dioica*, we have designated bryodin 2, to methods of producing bryodin 2 by conventional biochemical or recombinant means, to compositions comprising the toxin, and to therapeutic methods utilizing the toxin as an immune conjugate or a toxin fusion molecule.

Bryodin 2 (BD2), a novel ribosome-inactivating protein, is isolated from the roots of *Bryonia dioica*. BD2 exhibits toxicity to cells similar to other plant ribosome-inactivating proteins, suggesting that it may be useful in the killing of cells, particularly if directed to a defined cell population by the ligand of a cell-specific molecule. Such ligands can include an antibody, a ligand of a cell-surface receptor (i.e., transferrin, heregulin, and others well known to the skilled artisan). BD2 can also be used in the construction of conjugates or fusion molecules comprising the ligand of a cell-specific molecule and the toxin which would be useful in the treatment of a disease state.

Purified bryodin 2 has been detected as a single band of approximately 27,000 o dalton molecular weight under both reducing and non-reducing conditions. BD2, therefore, comprises a single chain polypeptide.

A partial primary structure of BD2 described herein has been determined by amino acid sequencing of various peptide fragments generated by specific chemical and enzymatic cleavage of BD2. Sequence analysis revealed that BD2 is a type I ribosome-inactivating protein having some similarity with, but distinct from, other ribosome-inactivating proteins of the Cucurbitaceae family including bryodin, trichosanthin and α-momorcharin (Montecucchi et al., 1989, *Int. J. Peptide Protein Res.* 33:263–267). All of these proteins display certain common properties characteristic of type I ribosome-inactivating proteins, such as being comprised of a single-peptide chain, a molecular weight of between 25 and 30 kDa and having an isoelectric point of approximately 9.0–10.0 (Stirpe and Barbieri, 1986, *FEBS Lett.* 196:1–8; Jimenez and Vasquez, D., 1985, *Ann. Rev. Microbiol.* 39:649–672).

The amino acid sequences have been confirmed by the cloning of the gene encoding bryodin 2 from the leaves of *Bryonia dioica*. A complete oligonucleotide sequence encoding mature BD2 and the putative signal sequence is provided in FIG. 13.

Bryodin 2 inhibits protein synthesis ($EC_{50}$=0.017 nM) in a cell-free in vitro translation assay using rabbit reticulocyte lysate. Also, BD2 is toxic to mice with $LD_{50}$ values of greater than 10 mg/kg when administered intravenously and about 8 mg/kg when administered intraperitoneally. Toxicity is most likely due to liver damage as seen histochemically by the presence of liver lesions and by an increased liver protein in a blood chemistry screen (data not shown). In comparison, the $LD_{50}$ of bryodin 1 has been reported to be 14.5 mg/kg, i.p. (Stirpe et al., 1986, *Biochem. J.* 240:659–665).

The production and use of derivatives, analogues, and peptides related to bryodin 2 are also envisioned and are within the scope of the present invention. Such derivatives, analogues, and peptides which exhibit ribosome-inactivating ability to inhibit protein synthesis can find uses and applications in the treatment of a wide variety of diseases. Such derivatives, analogues, or peptides can have enhanced or diminished biological activities in comparison to native BD2.

BD2-related derivatives, analogues, and peptides of the invention can be produced by a variety of means known in the art. Procedures and manipulations of both the genetic and protein levels are within the scope of the present invention.

Bryodin 2 is produced by cells of the root, leaves, and berries of *Bryonia dioica* and can be purified to homogeneity from extracts of plant tissue. Methods used to purify bryodin 2 are those commonly used in biochemistry and can include various combinations of centrifugation, chromatography, and polyacrylamide gel electrophoresis. The chromatography methods used can include, but are not limited to, combinations of ion exchange, gel permeation, and affinity chromatography. Affinity interactions including hydrophobicity, immunoaffinity or other affinity interactions are considered as part of the present invention. All of the chromatography methods can include both low pressure and high pressure methodologies.

Alternatively, BD2 can be produced by recombinant DNA techniques or chemical synthetic methods. To produce BD2 by recombinant methods, messenger RNA (mRNA) for the preparation of complementary DNA (cDNA) can be obtained from cell sources that produce BD2, whereas genomic sequences for BD2 can be obtained from any cells of *Bryonia dioica* regardless of tissue type. For example, roots of *B. dioica* can be utilized either as the source of the coding sequences for BD2 and/or to prepare cDNA or genomic libraries. Genetically-engineered microorganisms or cell lines transformed or transfected with total DNA or RNA from a source line can be used as a convenient source of DNA for screening.

Either cDNA or genomic libraries can be prepared from DNA fragments generated using techniques well known in the art. The fragments which encode BD2 can be identified by screening the prepared libraries with a nucleotide probe which would encode an amino acid sequence homologous to a portion of the BD2 amino acid sequence in FIG. 5 (Sequence ID#s 1–8). Although portions of the coding sequence may be utilized for cloning and expression, full length clones, i.e., those containing the entire coding region for BD2, may be preferable for expression. To these ends, techniques well known to those skilled in the art for the isolation of DNA, generation of appropriate fragments, by various methods, construction of clones and libraries, and screening recombinants can be used. See, for example, the techniques described in Sambrook et al., 1989, *Molecular Cloning, A Laboratory Manual,* 2nd Ed., Cold Spring Harbor Laboratory, New York.

Due to the degeneracy of the nucleotide coding sequences, alternative DNA sequences which encode analogous amino acid sequences for a BD2 gene can be used in the practice of the present invention for the cloning and expression of BD2. Such alterations include deletions, additions or substitutions of different nucleotide residues resulting in a sequence that encodes the same or a functionally equivalent gene product. (See Example 9, and Table 3 for specific probes.) The gene product may contain deletions, additions or substitutions of amino acid residues within the sequence, which result in a silent change thus producing a bioactive product. Bioactivity in this context is measured by the ability of the gene product to inhibit protein synthesis.

Any amino acid substitutions can be made on the basis of similarity in polarity, charge, solubility, hydrophobicity/ hydrophilicity and/or the amphipathic nature of the residue involved. For example, negatively charged amino acids include aspartic and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

In order to express a biologically active bryodin 2, the nucleotide sequence encoding BD2, or a functionally equivalent nucleotide sequence, is inserted into an appropriate vector, i.e., a vector which contains the necessary elements for the transcription and translation of the inserted coding sequence. Modified versions of the BD2 sequence can be engineered to enhance stability, production, purification, yield or toxicity of the expressed product. For example, the expression of a fusion protein or a cleavable fusion protein comprising BD2 and a heterologous protein can be engineered. Such a fusion protein can be designed so that the fusion protein can be readily isolated by affinity chromatography; e.g., by immobilization on a column specific for the heterologous protein. Where a cleavage site is engineered between the BD2 moiety and the heterologous protein, the BD2 protein can be released from the chromatographic column by treatment with an appropriate enzyme or agent that disrupts the cleavage site (e.g., see Booth et al., 1988, *Immunol. Lett.* 19:65–70; and Gardella et al., 1990, *J. Biol. Chem.* 265:15854–15859).

Methods which are well known to those skilled in the art can be used to construct expression vectors containing a BD2 coding sequence and appropriate transcriptional/translational control signals. These methods include in vitro recombinant DNA techniques, synthetic techniques and in vivo recombination/genetic techniques. See, for example, the techniques described in Sambrook et al., 1989, *Molecular Cloning: A Laboratory Manual,* 2nd Ed., Cold Spring Harbor Laboratory, New York.

A variety of host-expression systems can be utilized to express the BD2 coding sequence. These include, but are not limited to, microorganisms, such as bacteria transformed with a recombinant bacteriophage DNA, plasmid DNA or cosmid DNA expression vector containing the BD2 coding sequence; yeast transformed with recombinant yeast expression vectors containing the BD2 coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the BD2 coding sequence. To use mammalian expression systems, the BD2 ribosome-inactivating activity would have to be blocked or masked until lysis of the host cell or secretion of BD2 into the culture medium to protect the host cell from the toxin effects of BD2 or a mutant host cell resistant to the bryodin must be used.

Depending on the host/vector system utilized, any of a number of suitable transcription and translation elements including constitutive and inducible promoters, transcription enhancer elements, transcription terminators, etc., can be used in the expression vector (see, e.g., Bitter et al., 1987, *Methods in Enzymol.* 153:516–544). For example, when cloning in bacterial systems, inducible promoters such as pL of bacteriophage λ; plac, ptrp, ptac (ptrp-lac hybrid promoter) and the like may be used. Promoters produced by recombinant DNA or synthetic techniques can also be used to provide for controlled and high level transcription of the inserted BD2 coding sequence.

In bacterial systems, a number of expression vectors can be advantageously selected depending upon the use intended for the BD2 expressed. For example, when large quantities of BD2 are desired, vectors which direct the expression of high levels of protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the BD2 may also be desirable. Such vectors adaptable to such manipulation include, but are not limited to, the pET series of *E. coli* expression vectors (Studier et al., 1990, *Methods in Enzymol.* 185:60–89).

In yeast, a number of vectors containing constitutive or inducible promoters can be used. For a review, see *Current Protocols in Molecular Biology,* Vol. 2, 1988, ed. Ausubel et al., Greene Publish. Assoc. & Wiley Interscience, ch. 13; Grant et al., 1987, "Expression and Secretion Vectors for Yeast," in *Methods in Enzymol.* 153:516–544; Glover, 1986, DNA Cloning, Vol. II, IRL Press, Wash., D.C., Ch. 3; and Bitter, 1987, "Heterologous Gene Expression in Yeast," in *Methods in Enzymol.* 152:673–684. A constitutive yeast promoter such as ADH or Leu2 or an inducible promoter such as GAL can be used ("Cloning in Yeast," ch. 3, R. Rothstein In: *DNA Cloning,* Vol. 11, A Practical Approach, Ed. D. M. Glover, 1986, IRL Press, Wash. D.C.). Alternatively, vectors can be used which promote integration of foreign DNA sequences into the yeast chromosome.

In cases where plant expression vectors are used, the expression of the BD2 coding sequence can be driven by a number of promoters. For example, viral promoters such as the 35S RNA and 19S RNA promoters of CaMV (Brisson et al., 1984, *Nature* 310:511–514), or the coat protein promoter to TMV (Takamatsuetal., 1987, *EMBO. J.* 6:307–311) can be used. Alternatively, plant promoters such as the small subunit of RUBISCO (Coruzzi et al., 1984, *EMBO J.* 3:1671–1680; Brogli et al., 1984, *Science* 224:838–843); or heat shock promoters, e.g., soybean hsp17.5-E or hsp17.3-B (Gurley et al., 1986, *Mol. Cell. Biol.* 6:559–565) can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, *Methods for Plant Molecular Biology,* Academic Press, New York, Section VIII, pp 421–463; and Guerson & Corey, 1988, *Plant Molecular Biology*, 2d ed., Blackie, London, Ch. 7–9.

Other expression systems such as insects and mammalian host cell systems are well known in the art, but would have to be modified or adapted to produce a toxic molecule. One potential approach to modification would be to isolate mutant insect or mammalian cell lines resistant to BD2, as mentioned above.

In addition to producing bryodin 2 by recombinant DNA techniques, BD2 can also be produced in whole or in part by solid phase chemical synthetic techniques based on the determined amino acid sequence (see, Creighton, 1983, *Protein Structures and Molecular Principles*, W. H. Freeman and Co., New York, pp. 50–60; Stewart and Young, 1984, *Peptide Synthesis*, 2d Ed., Pierce Chemical Co.). This approach may be particularly useful in generating segments or fragments of BD2 corresponding to one or more of its biologically active regions.

Also within the scope of the present invention is the production of polyclonal and monoclonal antibodies which recognize bryodin 2 or related proteins.

Various procedures known in the art may be used for the production of polyclonal antibodies to epitopes of BD2. For the production of antibodies, various host animals can be immunized by injection with the BD2 protein, or as BD2 peptide, including but not limited to, rabbits, hamster, mice, rats, etc. Various adjuvants can be used to increase the immunological response, depending on the host species, including but not limited to, is Freund's (complete and incomplete); mineral gels, such as aluminum hydroxide; surface active substances, such as lysolecithin, plutohie polyols, polyanions, oil emulsions, keyhole limpet hemocyanin, dinitrophenol, and others well know to the skilled artisan.

A monoclonal antibody immunologically specific for an epitope of BD2 can be prepared by using any of a number of techniques known to the skilled artisan which provides for the production of antibody molecules by continuous cell lines in culture. These include, but are not limited to, the hybridoma technique originally described by Kohler and Milstein (1975, *Nature*, 256:495–497), and more recent modifications of those techniques.

Antibody fragments which contain the idiotype of the molecule can be generated by known techniques. For example, such fragments include, but are not limited to: the F(ab')$_2$ fragments generated by pepsin digestion of the antibody molecule and the Fab fragments which can be generated by reducing disulfide bridges of the F(ab')$_2$ fragments.

In another aspect of the present invention, the bryodin 2, or a functional equivalent, can be used with a ligand for a cell surface receptor to target the toxin to a specific cell population as a toxin-ligand conjugate.

The skilled artisan understands the term "ligand" includes within its scope any molecule that specifically binds or reactively associates or complexes with a receptor or other receptive moiety associated with a given target cell population. This cell-reactive molecule, or ligand, to which the toxin is linked via a linker in the conjugate, can be any molecule that binds to, complexes with or reacts with the cell population sought to be therapeutically or otherwise biologically affected. The cell-reactive molecule acts to deliver the toxin to the particular target cell population with which the ligand reacts. Such molecules include, but are not limited to, large molecular weight proteins (generally greater than 10,000 daltons) such as, for example, antibodies or adhesion molecules, smaller molecular weight proteins (generally, less than 10,000 daltons), polypeptides, or peptide ligands, and non-peptidyl ligands.

The non-immunoreactive protein, polypeptide, or peptide ligands which can be of use to form the conjugates of the present invention may include, but are not limited to, transferrin, epidermal growth factors, bombesin, gastrin, gastrin-releasing peptide, platelet-derived growth factor, IL-2, IL-6, or tumor growth factors, such as TGF-$\alpha$ and TGF-$\beta$. Non-peptidyl ligands may include, for example, steroids, carbohydrates and lectins.

The immunoreactive ligands comprise an antigen-recognizing immunoglobulin (or antibody), or antigen-recognizing fragment thereof. Particularly preferred immunoglobulins are those immunoglobulins which can recognize a tumor-associated antigen capable of internalization. As used, "immunoglobulin" may refer to any recognized class or subclass of immunoglobulin such as IgG, IgA, IgM, IgD or IgE. Preferred are those immunoglobulins which are within the IgG class of immunoglobulins. The immunoglobulin can be derived from any species. Preferably, however, the immunoglobulin is one of human or murine origin. Further, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments include, for example, the Fab', F(ab')$_2$, Fv or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing immunoglobulin fragments are well known to those skilled in the art. See generally, Parham, 1983, *J. Immunol.* 131:2895; Lamoye et al., 1983, *J. Immunol. Methods* 56:235; Parham, 1982, *J. Immunol. Methods* 53:133 and Matthew et al., 1982, *J. Immunol. Methods* 50:239.

The immunoglobulin can also be "chimeric" as that term is recognized in the art. Also, the immunoglobulin can be a "bifunctional" or "hybrid" antibody, that is, an antibody which may have one "arm" having a specificity for one antigenic site, such as a tumor-associated antigen, while the other arm recognizes a different target, for example, a second cell type-specific receptor molecule. In any case, the hybrid antibodies have a dual specificity, preferably with one or more binding sites specific for a target antigen, for example, an antigen associated with a tumor, an infectious organism, or other disease state.

Bifunctional antibodies are described, for example, in European Patent Publication EPA 0 105 360. Such hybrid or bifunctional antibodies may be derived, as noted, either biologically by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT application WO83/03699, published Oct. 27, 1983, and European Patent Publication, EPA 0 217 577, published Apr. 8, 1987, both of which are incorporated herein by reference.

In addition, the immunoglobulin may be a single chain antibody ("SCA"). These can consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dAbs) which possess antigen-binding activity. See, e.g., Winter and Milstein, 1991, *Nature* 349:295; Glockshaber et al., 1990, *Biochemistry* 29:1362 and Ward et al., 1989, *Nature* 341:544.

A preferred embodiment of an immunological ligand as part of a ligand/toxin conjugate for use in the present invention is a chimeric monoclonal antibody, preferably those chimeric antibodies which have a specificity toward a tumor-associated antigen. As used herein, the term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred in certain applications of the present invention, particularly human therapy. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison et al., 1984, *Proc. Natl. Acad Sci. USA* 81:6851; U.S. Pat. Nos: 5,202,238, and 5,204,244.

Encompassed by the term "chimeric antibody" is the concept of "humanized antibody," that is, those antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann et al., 1988, *Nature* 332:323; and Neuberer et al., 1985, *Nature* 314:268. Particularly preferred CDRs correspond to those representing sequences recognizing the antigens noted above for chimeric and bifunctional antibodies.

One skilled in the art will recognize that a bifunctional chimeric antibody can be prepared which would have the benefits of lower immunogenicity of the chimeric or humanized antibody, as well as the flexibility, especially for therapeutic uses, of the bifunctional antibody described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized or an antigen-recognizing fragment or derivative thereof.

Further, as noted above, the immunoglobulin, or fragment thereof, used in the present invention may be polyclonal or monoclonal in nature. Monoclonal antibodies are the preferred immunoglobulins, however. The preparation of such polyclonal or monoclonal antibodies now is well know to those skilled in the art who are fully capable of producing useful immunoglobulins which can be used in the present invention. See, e.g., Kohler and Milstein, 1975, *Nature* 256:495. In addition, hybridomas and/or monoclonal antibodies which are produced by such hybridomas and which are useful in the practice of the present invention are publicly available from such sources as the American Type Culture Collection (ATCC), 12301 Parklawn Drive, Rockville, Md. 20852, or commercially, for example, from Boehringer-Mannheim Biochemicals, P.O. Box 50816, Indianapolis, Ind. 46250.

A particularly preferred monoclonal antibody of the present invention is one that binds a tumor-associated cell surface antigen and is capable of internalization. In a particular embodiment of the present invention, the toxin is conjugated to the chimeric antibody BR96 ("chiBR96"), disclosed in U.S. Ser. No. 07/544,246, filed Jun. 26, 1990, and which is equivalent to PCT Published Application, WO91/00295, published Jan. 10, 1991. ChiBR96 is an internalizing murine/human chimeric antibody and is reactive with a fucosylated Lewis Y antigen expressed by human carcinoma cells, such as those derived from the breast, lung, colon, and ovarian carcinomas. The hybridoma expressing chimeric BR96 and identified as the chiBR96 was deposited on May 23, 1990 under the terms of the Budapest Treaty, with the American Type Culture Collection, and designated ATCC HB10460.

One of the preferred methods of making an immunotoxin of the present invention is by chemically conjugating the bryodin 2 toxin with the ligand, preferably a monoclonal antibody or a fragment thereof, as described above. Many methods of chemical conjugation are well known to the skilled artisan. See, e.g., Vitetta et al., 1987, *Science* 238:1098; Pastan et al., 1986, *Cell* 47:641; and Thorpe et al., 1987, *Cancer Res.* 47:5924). These methods generally conjugate the toxin and the antibody by means of cross-linking agents that introduce a disulfide bond between the two proteins. Immunotoxins which have been prepared with nonreducible linkages have been shown to be consistently less cytotoxic than similar toxins cross-linked by disulfide bonds.

One preferred method uses N-succinimidyl-3-(2-pyridyldithio)-propionate (SPDP) and 2-iminothiolane hydrochloride (2IT). Other preferred reagents are sodium S-4-succinimidyioxycarbonyl-α-methyl benzyl thiosulfate (SMBT) and 2IT or succinimidyloxy carbonyl-α-methyl-α(2-pyridyldithio)-toluene and 2IT. Each group of reagents introduces a disulfide bond between the toxin and the antibody which is reducible, but the bond is also resistant to breakdown providing stability of the conjugate in vitro and in vivo. Upon internalization into lyso somes or endosomes by the target cell, the bond is reduced and the toxin enters the cytoplasm, binds elongation factor 2, disrupting protein synthesis.

Another preferred embodiment of the present invention is recombinant immunotoxins, particularly single-chain immunotoxins. These molecules have the advantage over toxin-antibody conjugates (immunotoxins) in that they are more readily produced than the conjugates, and homogeneous populations of toxin molecules are generated, i.e., single peptide composed of the same amino acid residues.

The techniques for cloning and expressing DNA sequences encoding the amino acid sequences corresponding to a single chain derivative of a parental antibody are well known to the skilled artisan, as discussed above. Methods for determining the nucleotide sequence and complete amino acid sequence of bryodin 2 are also described above. Various methods of constructing recombinant toxin fusion proteins are described in Pastan and Fitzgerald, 1991, *Science* 254, 1173; Siegall et al., 1988, *Proc. Natl. Acad. Sci. USA* 85:9738; Batra et al., 1991, *Mol. Cell Biol.* 11:2200; O'Hare et al., 1990, *FEBS Lett.* 273:200; Westby et al., 1992, *Bioconj. Chem.* 3:375.

The plant ribosome-inactivating toxin, bryodin 2, of the present invention is useful for therapeutic applications, both in vitro and in vivo in its isolated form and as ligand-toxin conjugates and recombinant toxin fusion proteins. Ribosome-inactivating proteins isolated from Cucurbitaceae plants have found use as, among others, abortifacients, immunomodulators, anti-tumor and anti-viral agents (Ng et al., 1992, *Gen. Pharmac.* 23:575–590) or as an anti-malerial agent (Amorim et al., 1991, *Mem. Inst. Oswaldo Cruz* 86:177).

Bryodin 2 is particularly useful as a ligand-toxin conjugate or a recombinant toxin fusion protein since BD2 is less toxin than many other protein toxins and ribosome-inactivating proteins that have been used to construct immunotoxins and is particularly potent at inhibiting protein synthesis once inside the cell. Ligand-toxin conjugate and recombinant toxin fusion proteins can be used for either in vivo treatment of cells removed from the body or a patient to remove or kill a desired cell population prior to reinfusion of the remaining cells back into the patient or directly administering the recombinant-toxin fusion into the patient.

For ex vivo uses, cells, such as bone marrow, may be removed from a patient suffering from cancer and the marrow purged by treatment with the ligand-toxin conjugate or fusion protein. Following treatment, the marrow is infused back into the patient (see, e.g., Ramsay et al., 1988, *J. Clin. Immunol.* 8:81–88).

For in vivo uses, the present invention provides a method for selectively killing cells, i.e., tumor cells, expressing the antigen that specifically binds the ligand, or functional equivalent of the ligand-toxin conjugate or fusion molecule. This method comprises reacting the toxin conjugate or fusion molecule with the tumor cell by administering to a subject a pharmaceutically effective amount of a composition containing at least one ligand-toxin conjugate or fusion molecule of the present invention.

In accordance with the present invention, the subject may be human, equine, porcine, bovine, murine, canine, feline, and avian. Other warm blooded animals are also included within the scope of the present invention.

The claimed invention also provides a method of inhibiting the proliferation of tumor cells, particularly mammalian tumor cells. This method comprises contacting the mammalian tumor cells with a proliferation inhibiting amount (i.e., effective amount) of a tumor targeted toxin joined to a ligand specific for a tumor-associated antigen so as to inhibit proliferation of the mammalian tumor cells.

In one example, bryodin 2 is conjugated to the chimeric monoclonal antibody BR96 (chiBR96) specific for the Lewis Y determinant and capable of internalizing within the tumor cells to which it binds. Tumor cells were contacted with the chiBR96-BD2 conjugates in vitro at various dosages to determine an amount of chiBR96-BD2 conjugate effective for cell killing. Effectiveness was determined in vitro by several methods known to one skilled in the art including cytotoxicity assays.

The subject invention further provides methods for inhibiting the growth of human tumor cells, treating a tumor in a subject, and treating a proliferative type disease in a subject. These methods comprise administering to the subject an effective amount of the composition of the invention. Extrapolation from mammalian model systems for diseases such as cancer can be difficult in some cases. But, animals do provide more than just a preliminary screen of potential therapeutic compositions. Each composition which is determined to have an effective dose in an animal model to inhibit the proliferation of or kill a target cell in vivo demonstrates that the composition is an active agent for inhibition or killing. One of skill in the art can and does use this information to provide a basis for testing a composition for effectiveness in humans. All compositions previously tested in animals demonstrated the requisite activity in humans. The only remaining question to be determined is any potential adverse effects from the composition particular to the human system and whether the composition is ultimately effective to prolong life or cure a patient.

It is apparent therefore that the present invention encompasses pharmaceutical compositions, combinations and methods for treating proliferative and infectious disease wherein a cell possesses a cell surface receptor associated with the disease state. For example, the invention includes pharmaceutical compositions for use in the treatment of human carcinomas, malaria, trypanosomiasis, inflammatory diseases and immunodeficiency. The composition can contain an antibody, or ligand for the antigen specific to the disease state, conjugated to bryodin 2 of the present invention. The composition can also include other ligands conjugated to bryodin 2 or other toxins, chemotherapeutic agents, drugs, enzymes, etc.

The toxin-ligand and fusion molecule compositions of the invention can be administered using conventional modes of administration, including but not limited to, intravenous, intraperitoneal, oral, intralymphatic or administration directly into the site of disease. Intravenous administration is preferred.

The compositions of the invention can be in a variety of dosage forms which include, but are not limited to, liquid solutions or suspension, tablets, pills, powders, suppositories, polymeric microcapsules or microvesicles, liposomes and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the composition should be titrated to the individual patient. Nevertheless, an effective dose of the compositions of this invention can be in the range of from about 1 to about 2000 mg/m$^2$.

The inter-relationship of dosages for animals of various sizes and species and humans based on mg/m$^2$ of surface area is described by Freireich et al., 1966, *Cancer Chemother. Rep.* 50:219–244. Adjustments in the dosage may be made to optimize the tumor cell growth inhibiting and killing response, doses may be divided and administered on a daily basis or the dose reduced proportionally depending upon the situation. It would be clear that the dose of the composition of the invention required to achieve the desired effect may be further reduced with schedule optimization.

In order that the invention described herein may be more fully understood, the following examples are set forth. It should be understood that these examples are for illustrative purposes only and are not to be construed as limiting the scope of this invention in any manner.

EXAMPLE 1

Purification of Bryodin 2 from *Bryonia dioica*

This example describes the preparation of total protein from the root of *Bryonia dioica* and the separation of the ribosome-inactivating proteins, including the novel protein bryodin 2.

*Bryonia dioica* roots (Poyntzfield Herb Nursery, Rossshire, Scotland) were cleaned, peeled, shred and homogenized using a Waring blender in phosphate-buffered saline (PBS, 1 liter PBS:550 g root material). The slurry obtained was stirred for 16 hours at 4° C. and strained through cheesecloth. After removal of the plant material, the filtrate was centrifuged at 15×g for 15 minutes at 4° C. to remove large particles and then centrifuged a second time at 50×g for 20 minutes to clarify. The supernatant was then filtered through a sterile 0.22 micron filter and dialyzed versus 5 mM sodium phosphate buffer, pH 6.5.

Figure 2:
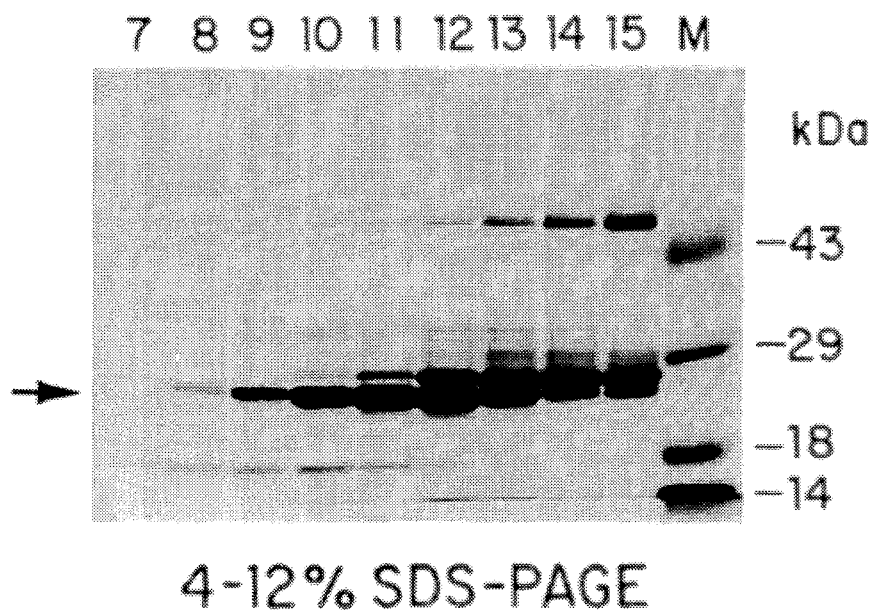
FIG. 2 is the result of SDS-PAGE analysis of fractions 19 through 27 from the CM-Sepharose chromatography separation. Lane M contains molecular weight standards: ovalbumin (43,000 mw), carbonic anhydrase (29,000 mw), β-lactoglobulin (18,000 mw), lysozyme (14,000 mw), bovine trypsin inhibitor (6,000 mw), and insulin (2,000 mw).

Plant proteins were then separated on the basis of their charge and size using a five-step procedure. First, the dialyzed root extract was applied to an anion exchange material CM-SEPHAROSE™ column (Pharmacia, Uppsala, Sweden), equilibrated to 5 mM sodium phosphate pH 6.5. Proteins were eluted from the column using a salt gradient of 0 to 0.3M NaCl. Second, 4 ml fractions were collected and the optical density of the effluent was monitored at 280 nm (FIG. 1 ). The chromatography fractions were then evaluated by electrophoresis. Fifteen µl aliquots of each collected fraction were added to SDS-PAGE sample buffer, boiled at 100° C. for 5 min. and separated on 4–12% SDS-PAGE gradient gels (Laemmili, 1970, *Nature* 227:680–685). The gels were then stained with Coomassie blue to resolve the separated proteins (FIG. 2).

Figure 3:
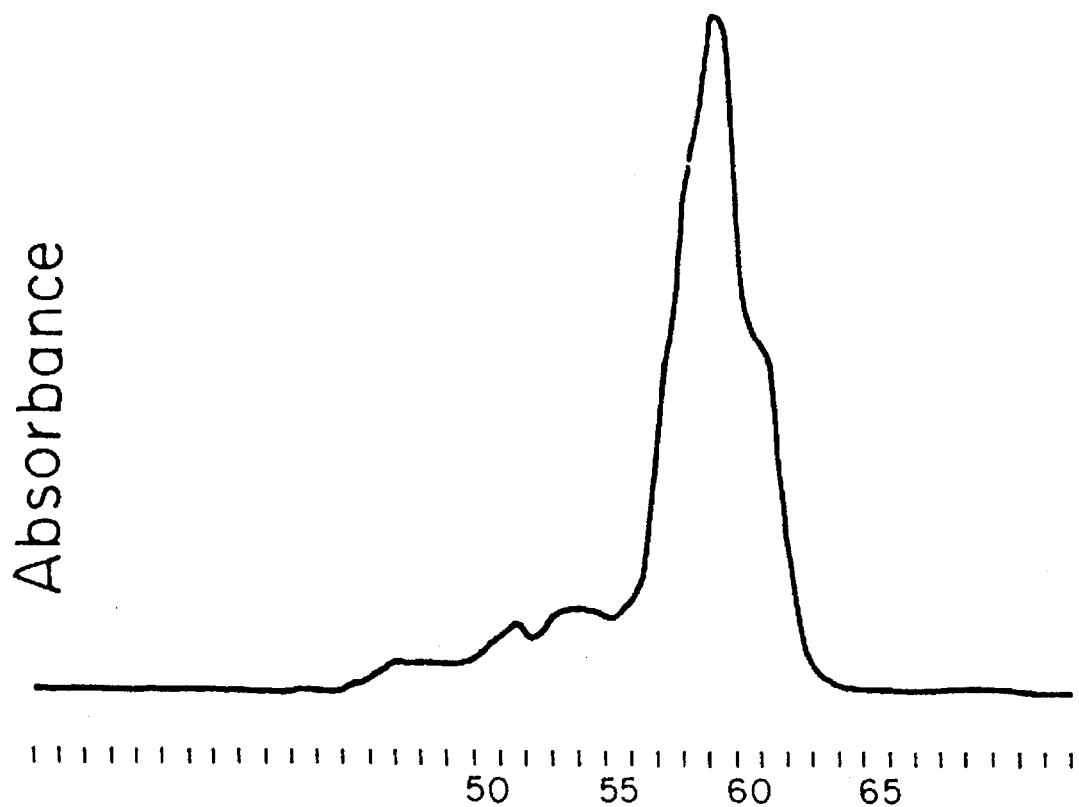
FIG. 3 is a chromatogram obtained from a TSK-3000 size exclusion column. Fractions containing the 27 kDa band were pooled from the CM-Sepharose chromatography separation and concentrated to less than 8 ml. The concentrate was applied to the column and absorbence monitored at 280 nm.
Figure 4:
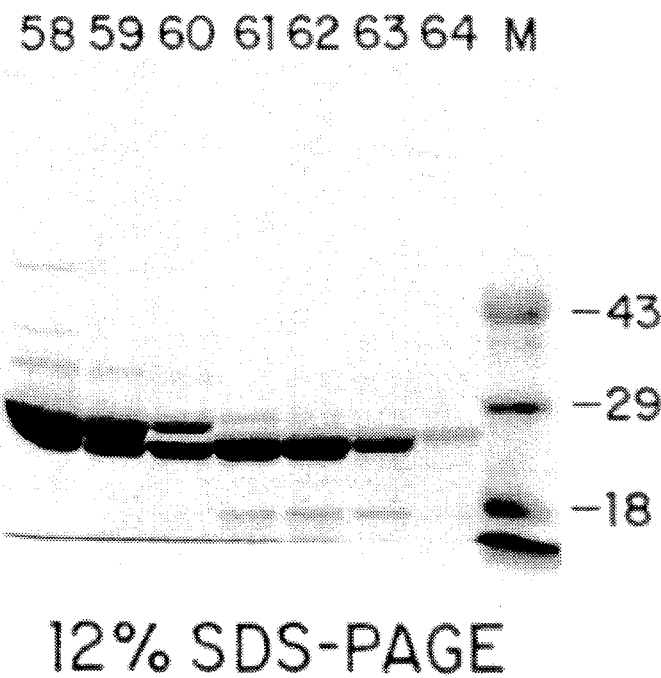
FIG. 4 illustrates the result obtained for SDS-PAGE analysis of fractions 58 through 64 from size exclusion chromatography of the partially purified bryodin. Lane M contains molecular weight standards: ovalbumin (43,000 mw), carbonic anhydrase (29,000 mw), and β-lactoglobulin (18,000 mw).

In the third step of the purification, fractions 9 through 15 which contained a 27 kDa protein band were pooled and then concentrated to a volume of less than 8 ml using a Centriprep 10 (Amicon, Bedford, Mass.). The fourth step was to apply the concentrate to a size-exclusion column TSK-3000 (TosoHaas, Inc., Philadelphia, Pa.) and then to elute the plant proteins isocratically. Three ml fractions were collected and the eluate was monitored at 280 nm (FIG. 3). Following size-exclusion chromatography, the fifth step in the purification process was to analyze the fractions by SDS-PAGE as described above, except that a 12% SDS-PAGE gel was used. Proteins were resolved by Coomassie blue staining. Two discrete protein bands migrating at 29 kDa and 27 kDa were observed in the peak fractions 58 through 64 (FIG. 4). These fractions were pooled separately and this material was used for further characterization.

EXAMPLE 2

Amino Acid Composition of Bryodin 2

In this example, the amino acid composition of the protein comprising the 27 kDa band designated bryodin 2 is determined and compared to the amino acid compositions of bryodin and bryodin-L. Amino acid analysis of electroblotted bryodin 2 was performed with the model 420A derivatizer/analyzer (Applied Biosystems, Inc.) after manual vapor phase hydrolysis with 6N HCl at 165° C. for 1 hr (Dupont et al., 1989 in Hugli, T. E., ed., Techniques in Protein Chemistry, pp. 284–294, Academic Press, Inc., San Diego, Cailf.). From this analysis it appears that bryodin 2 is a novel bryodin ribosome-inactivating protein significantly different from bryodin and bryodin-L.

TABLE 1

|       | bryodin 1[1] (residues/mol) | byrodin L[1] (residues/mol) | bryodin 2 (residues/mol) |
|-------|---------|---------|---------|
| Lys   | 8.6     | 10.8    | 0.4     |
| His   | 1.9     | 1.0     | abs     |
| Arg   | 11.8    | 11.0    | 8.5     |
| Asx   | 22.5    | 25.5    | 14.0    |
| Thr   | 15.1    | 17.4    | 13.1    |
| Ser   | 30.2    | 24.4    | 6.5     |
| Glx   | 17.7    | 18.9    | 38.2    |
| Pro   | 6.7     | 7.2     | 15.0    |
| Gly   | 11.4    | 11.4    | 16.1    |
| Ala   | 22.4    | 24.1    | 28.7    |
| 1/2 cys | 0.24  | abs[2]  | abs     |
| Val   | 15.6    | 14.4    | 34.2    |
| Met   | 1.6     | 2.2     | abs     |
| He    | 15.1    | 15.4    | 23.3    |
| Leu   | 28.3    | 24.5    | 28.3    |
| Tyr   | 14.2    | 11.7    | 5.0     |
| Phe   | 8.3     | 7.4     | 18.5    |
| Trp   | 2.0     | abs     | ND[3]   |

[1]Values for amino acid residues taken from European Publication Number EPO 390 040.
[2]abs means the amino acid residue was either not present or was present in amounts below detection.
[3]ND, not determined.

EXAMPLE 3

N-Terminal Amino Acid Sequence Analysis of Bryodin

In this example, the N-terminal amino acid sequence of the 27 kDa and 29 kDa proteins contained in the pooled fractions was determined. The first 32 amino acid residues of the 27 kDa and 29 kDa protein bands were unambiguously determined. The protein comprising the 29 kDa band was found to be identical to the bryodin (bryodin 1) described by Stirpe. The protein comprising the 27 kDa band was found to have an N-terminal amino acid sequence substantially different from the N-terminal sequence of bryodin 1 (FIG. 5). We have designated the novel toxin bryodin 2.

N-terminal amino acid sequences were determined by using the following methods which are briefly described. The protein bands were individually recovered from SDS-polyacrylamide gels by electroblotting onto a Problott membrane (Applied Biosystems, Foster City, Calif.) using a Mini-transblot Electrophoretic Transfer Cell (Bio Rad Laboratories, Richmond, Calif.) (Matsudaira, 1987, *J. Biol. Chem.* 262: 10035–10038). The membrane was stained with Coomassie brilliant blue, then destained, and the 29- and 27-kDa bands were excised for subsequent amino terminal sequence analysis.

Samples were sequenced in a pulsed liquid phase protein sequencer (Model 476A, Applied Biosystems) equipped with a vertical cross-flow reaction cartridge using manufacturer's released cycle programs. Phenylthiohydantoin amino acid derivatives were analyzed by reversed-phase ltPLC with a PTH C18 column (Applied Biosystems) using sodium acetate/tetrahydrofuran/acetonitrile gradient for elution (Tempst and Reviere, 1989, *Anal Biochem.* 183:290–300). Data reduction and quantitation were performed using a Model 610A chromatogram analysis software (Applied Biosystems).

The amino-terminal amino acid sequence of BD2 was performed with 47 pmoles (based on the initial yield of identified Val-1 ), electroblotted onto Problott membrane. A single amino acid sequence was obtained and unambiguous identification of PTH-amino acid derivatives was possible up to residue 32 (FIG. 5; SEQ ID #1).

EXAMPLE 4

Determination of the Amino Acid Sequence of Peptide Fragments of Bryodin 2

In this example, the 27 kDa protein (BD2) isolated by PAGE was cleaved into fragments using cyanogen bromide and various proteinases. The peptide fragments were isolated and the amino acid sequence of certain fragments determined. The obtained amino acid sequences were analyzed for overlaps and homology with known ribosome-inactivating proteins.

BD2 was cleaved with cyanogen bromide by dissolving BD2 into 30 gl of 70% formic acid and adding enough cyanogen bromide (30 mg/100 gl) in 70% formic acid to provide a 1,000-fold molar excess over methionine. The reaction was allowed to proceed under a nitrogen cushion for 4 hours at 30° C. and for an additional 18 hours at 22° C. in the dark. The cyanogen bromide peptides were separated by gel permeation chromatography using a 600×7.5 mm Bio-Sil TSK-250 column (Bio-Rad Laboratories, Richmond, Calif.) equilibrated in 0.1% TFA containing 40% acetonitrile at a flow rate of 250 ×l/min. The eluent was monitored at 280 nm and peaks were collected manually for further analysis.

Purified BD2 or purified cyanogen bromide peptides derived from BD2 were cleaved with the proteinases trypsin (L-(tosylamido-2-phenyl)ethyl chloromethyl ketonetreated, Worthington), Lys-C and Glu-C (*Staphylococcus aureus*, Boehringer Mannheim). Protease cleavages were done in 40 µl 0.1M Tris-acetic acid buffer containing 2M urea, pH 8.5, at 37° C. for 16 hours. The enzyme substrate ratio was 1 to 25. The enzymatic digests were acidified with 10% TFA to pH 2 and separated by reversed phase HPLC.

Reversed phase HPLC was carried out using a 2.1×100 mm RP-300 cartridge column (Applied Biosystems) and a 1×100 mm C18 Vydac column (The Nest Group) at a flow rate of 100 µl/min and 40 µl/min, respectively, at 40° C. Linear acetonitrile gradients from solvent A (0.1% TFA in water) to solvent B (0.09% TFA in acetonitrile) were used for elution. The eluent was monitored at 215 nm and peaks were collected manually.

Peptides were sequenced on polybrene-coated glass fiber discs (Applied Biosystems). Automated sequence analysis was performed in a pulsed-liquid protein sequencer model 476A (Applied Biosystems) using manufacturer-released cycle programs. PTH-amino acid derivatives were analyzed by reversed-phase HPLC with a PTH C18 column (Applied Biosystems) using a sodium acetate/tetrahydrofuran/acetonitrile gradient for elution. Data reduction and quantitation were performed on a Macintosh IIsi computer (Apple Computer, Inc.) and model 610A chromatogram analysis software (Applied Biosystems).

Edman degradation of selected fragments derived from BD2 by cleavage with trypsin, cyanogen bromide and further digestion with Lys-C and Glu-C protease are shown in FIG. 6. Cleavage of BD2 with cyanogen bromide generated two major peptides (M2 and M4). Peptide M2 ($M_R$=14,000) was the aminoterminal cyanogen bromide peptide of BD2 (SEQ ID NO: 1) and is shown in FIG. 6. Peptide M4 ($M_R$=12,000) represents the carboxylterminal cyanogen bromide peptide of BD2. The aminoterminal amino acid sequence of M4 is shown in FIG. 6 (SEQ ID NO: 4).

Digestion of M4 with Lys-C protease generated three major fragments. The amino terminal sequences of two of those fragments, designated M4/K2 (SEQ ID NO: 5) and M4/K11 (SEQ ID NO: 6), are shown in FIG. 6. Peptide M4/K11 was subfragmented with Glu-C protease, generating four fragments. Peptide E4 (SEQ ID NO: 7) provided overlap information and extended the sequence of M4/K11 by 14 residues.

Peptide M4, preceded by a methionine residue, provided an overlap with peptides T21 (SEQ ID NO: 3) and K2 (SEQ ID NO: 5), extending the sequence of M4 by 25 residues.

BD2 belongs to a family of plant ribosome-inactivating proteins, including momordin, shiga toxin a-chain, shiga-like toxins I and II, and ricin A-chain. A comparison of the amino acid sequences of BD2 and momordin II is shown as an example in FIG. 7. Peptides T10 (SEQ ID NO: 2) and M4/K11 (SEQ ID NO: 6) were aligned with the momordin sequence (SEQ ID NO: 13) based on similarity, without providing overlap information with T21 and M4/K2, respectively. BD2 shared with momordin 77 amino acid residues out of 157 comparisons (49.0% identity).

EXAMPLE 5

Determination of Protein Synthesis Inhibition Activity

In this example, the ability of BD2 to inhibit protein synthesis was determined in a cell-free rabbit reticulolysate translation system. Bryodin 2 was found to be a very efficient inhibitor of protein synthesis, having activity similar to that of bryodin 1 and substantially more active than gelonin or ricin A chain.

Protein synthesis inhibition activity was determined using a cell-free rabbit reticulocyte lysate translation system (Promega Biotec, Madison, Wis.). The assay was performed as per the manufacturer's instructions. Briefly, toxin proteins were mixed in a volume of 25 µl per reaction with rabbit reticulocyte lysate (70% of reaction volume), a mixture of all amino acids (minus leucine) at 1 nM, RNasin ribonuclease inhibitor (20U), 0.5 mCi/ml [$^3$H]-leucine, and RNA substrate (0.5 µg). The reaction was incubated at 30° C. for 5 minutes and terminated by adding 1M NaOH with 2% $H_2O_2$. The translation product was precipitated using ice-cold 25% trichloroacetic acid (TCA) with 2% casamino acids on ice for 30 minutes. The radiolabeled proteins were harvested on glass fiber filters, rinsed with cold 5% TCA, rinsed with acetone and then dried. The amount of protein translated was quantitated using a scintillation counter.

Both isolated protein toxins bryodin 1 and bryodin 2 were found to be potent inhibitors of protein synthesis with $EC_{50}$ values of 0.007 and 0.017 nM, respectively. In the same assay, gelonin, a type 1 ribosome-inhibiting protein, was found to have an $EC_{50}$ value of 0.049 nM and ricin A chain was found to have an $EC_{50}$ value of 0.059 nM.

EXAMPLE 6

Isolation of Monoclonal Antibodies Specific for Bryodin 2

In this example, murine monoclonal antibodies are generated specific for bryodin 2. Antibodies were generated which were not cross-reactive with bryodin 1 or with control protein toxins ricin A chain, momordin or gelonin.

Briefly, four-to-six-week-old female BALB/c mice were initially immunized with two subcutaneous injections (0.1 ml) and one intraperitoneal injection (0.2 ml) of a 50:50 mixture of purified BD proteins (BD1 and BD2; 200 µg total protein) and Ribi adjuvant with ISA 50 Seppic Oil (Ribi Immunochemical, Hamilton, Mont.), followed by a 0.3 ml intraperitoneal injection of BD protein, 60 µg, in ISA 50 Seppic Oil, on week four. Another 0.3 ml intraperitoneal injection of 60 µg BD protein was given on week seven to boost immunization.

Spleen cells from an immunized mouse were removed three days after the final immunization and fused with the myeloma Ag8.653 at a ratio of 3:1. with 40% polyethylene glycol 1450. The fused mixture was plated in HAT (hypoxanthine-aminopterin-thymidine) medium with approximately $2 \times 10^6$ thymocytes/ml (BALB/c) at 0.2 ml/well into 10 96-well plates. Hybridomas secreting antibodies specific for BD2 were selected by ELISA using plates coated with BD2. Briefly, Iratoulon II plates (Dynatech, Chantilly, Va.) were coated with 0.3 µg/ml BD1 or BD2 overnight at 4° C. in 0.1 ml/well carbonate buffer (0.1M sodium carbonate/sodium bicarbonate, pH 9.6). Plates were washed with phosphate-buffered saline (PBS), blocked with 200 µl/well Specimen Diluent (Genetic Systems Corp., Redmond, Wash.) for 2 hours at 4° C., and rewashed with PBS. Sample supernatant from wells containing growing clones and Specimen Diluent (0.05 ml each) were added to each well, incubated at 4° C. for 2 hours, and washed three times in PBS. Goat anti-mouse horseradish peroxidase (HRP) (0.1 ml/well), used at 1:3,000 dilution in Conjugate Diluent (Genetic Systems Corp.), was incubated for 1 hour at room temperature and washed four times before addition of 0.1 ml/well substrate (tetramethyl benzedine in substrate buffer, Genetic Systems) and further incubated for 10 minutes. The reaction was stopped with 0.1 ml/well 1.3M $H_2SO_4$ and the optical density quantified at 450 nm on a Bio-Tek microplate reader (Winooski, Vt.).

Hybridomas secreting anti-BD2 antibodies were selected and cloned by two rounds of limiting dilution and retested for reactivity by ELISA as described above. Limiting dilutions were carried out in IMDM, 10% fetal calf serum, 1% penicillin/streptomycin. Two BD2-reactive antibodies were selected and purified from culture supernatant by affinity chromatography using Gamma Bind Plus (Pharmacia). Protein concentration was determined by $OD_{280}$.

Figure 8:
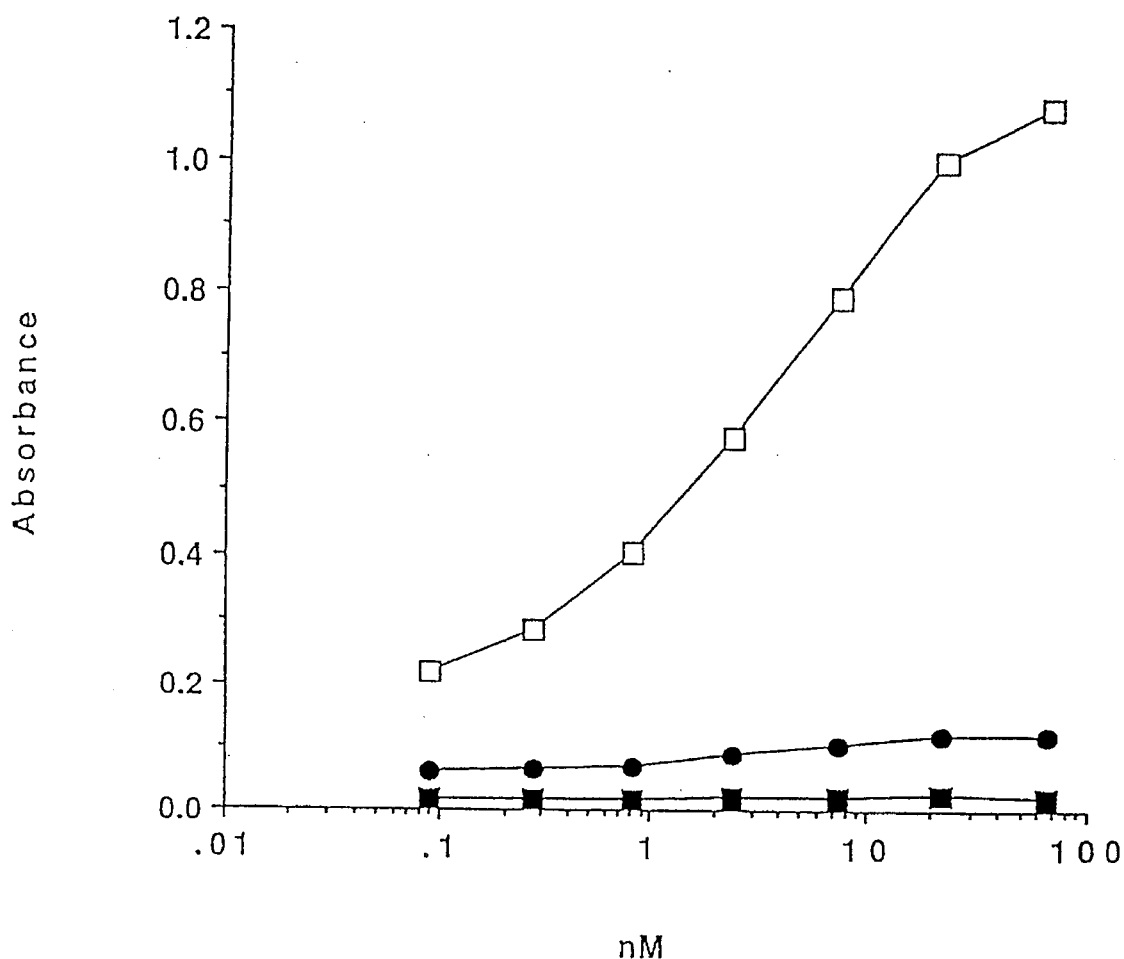
FIG. 8 illustrates ELISA binding of anti-BD2 antibody (50-44-3) to immobilized ribosome-inactivating proteins. Detection was done with goat anti-mouse IgG1 HRP. BD2 (□), BD 1 (●), ricin A chain (■).

Specificity assays for the two selected anti-BD2 antibodies were performed using the ELISA assay described above with BD2 except that, in addition, assays using ricin A chain or gelonin were coated onto the ELISA plate at 0.3 µg/ml. Detection of bound antibody was done with goat anti-mouse IgG1-HRP at 1:1000 dilution (Southern Biotechnology, Birmingham, Ala.). As shown in FIG. 8, monoclonal antibody 50-44-3 recognized BD2, but not BD1 or ricin A chain. The slight reactivity with BD1 is most likely attributable to a small amount of BD1 contamination present in the BD2 preparation. Additionally, 50-44-3 did not react or recognize MMC or gelonin (data not shown). A second antibody, 50-43-1, was also isolated which has a specificity similar to 50-44-3 (data not shown). This second antibody appears only to differ in having a lower affinity or avidity for BD2.

EXAMPLE 7

Toxicity of Bryodin 2 in vivo

In this example, the single dose $LD_{50}$ was determined for bryodin 2 in mice. It was determined that a dose of 8 mg/kg intraperitoneally or greater than 10 mg/kg administered intravenously was sufficient to kill half the mice tested. The single dose $LD_{50}$ for bryodin is reported to be 14.5 mg/kg when administered intraperitoneally.

Briefly, toxicity was determined by both intraperitoneal and intravenous (via the tail vein) injection. The purified toxin was diluted in phosphate buffered saline to reach final administered doses of 3 to 20 mg/kg. Mice (type) were placed in groups of 2–4 and administered a quantity of toxin. Animals were monitored for at least 14 days following injection of toxin. For comprehensive necropsy analysis, animals were intravenously injected with 20 mg/kg toxin, sacrificed after 24 hours, and selected tissues were analyzed using gross and microscopic techniques.

Bryodin 2 was determined to be slightly more toxic to mice than bryodin 1 when administered intraperitoneally and when administered intravenously (Table 2). Comprehensive necroscopy determined that liver toxicity was the cause of death in animals receiving a lethal dose of toxin. Histochemical analysis of tissue from injected animals showed liver lesions. Additionally, SGOT and SGPT were elevated in these animals.

TABLE 2

Lethal Toxicity Of BD1 and BD2 to Mice

| RIP | Route | Dose (mg/kg) | # Mice | % Survival |
| --- | --- | --- | --- | --- |
| BD2 | i.v. | 5 | 4 | 100% |
|  | i.v. | 6 | 4 | 100% |
|  | i.v. | 7 | 4 | 100% |
|  | i.v. | 8 | 4 | 75% |
|  | i.v. | 10 | 4 | 75% |
|  | i.v. | 12 | 2 | 0% |
|  | i.v. | 14 | 2 | 0% |
| BD1 | i.v. | 12 | 4 | 100% |
|  | i.v. | 12 | 4 | 100% |
|  | i.v. | 16 | 2 | 100% |
|  | i.v. | 18 | 2 | 100% |
|  | i.v. | 20 | 2 | 100% |
| BD2 | i.p. | 7 | 4 | 100% |
|  | i.p. | 8 | 6 | 50% |
|  | i.p. | 10 | 2 | 0% |
|  | i.p. | 12 | 2 | 0% |
| BD1 | i.p. | 10 | 4 | 100% |
|  | i.p. | 12 | 2 | 100% |
|  | i.p. | 14 | 2 | 100% |
|  | i.p. | 16 | 2 | 100% |

Animals (20–25 g) were observed for >14 days following injection. BD RIP was diluted in PBS prior to injection.

EXAMPLE 8

Chemical Conjugation of Bryodin 2 to Form an Immunotoxin

In this example, bryodin 2 was covalently crosslinked (or conjugated) to a chimeric monoclonal antibody immunologically reactive with a highly specific tumor-associated antigen, chimetic BR96 (ATCC HB 10460). The antibody was intended to direct the ribosome-inactivating protein to the target tumor cell and to protect the patient from the inherent toxicity of the RIP. Activity of the immunotoxin was determined by testing the ability of the immunotoxin to bind antigen on membranes isolated from a breast carcinoma cell line and a determination of the ability of the immunotoxin to kill the same cell line. Partially purified immunotoxin has been shown to bind to the membranes of a human breast carcinoma cell line (H3396) known to be BR96 positive and to be toxic to these cells.

Chimeric BR96 (15.6 mg/ml) was thiolated with the addition of a three-fold molar excess of 2-Iminothiolane (2-IT, Pierce Chemical Company, Rockford, Ill.) in 0.2M sodium phosphate buffer (pH 8.0), 1 mM EDTA for 1 hour at 37° C. Unreacted 2-IT was removed by chromatography through a PD-10 column (Pharmacia). BD2 (4.6 mg/ml) was derivatized with a three-fold molar excess of succinimidy-loxycarboxyl-α-methyl-α(2-pyridyldithio)-toluene (SMPT) in 0.2M sodium phosphate buffer, pH 8.0, 1 mM EDTA at room temperature for 60 minutes followed by chromatography on a PD-10 column. The modified toxin and thiolated antibody were mixed in a 5:1 molar ratio and incubated at room temperature for 16 hours to allow disulfide bond formation.

Figure 9A:
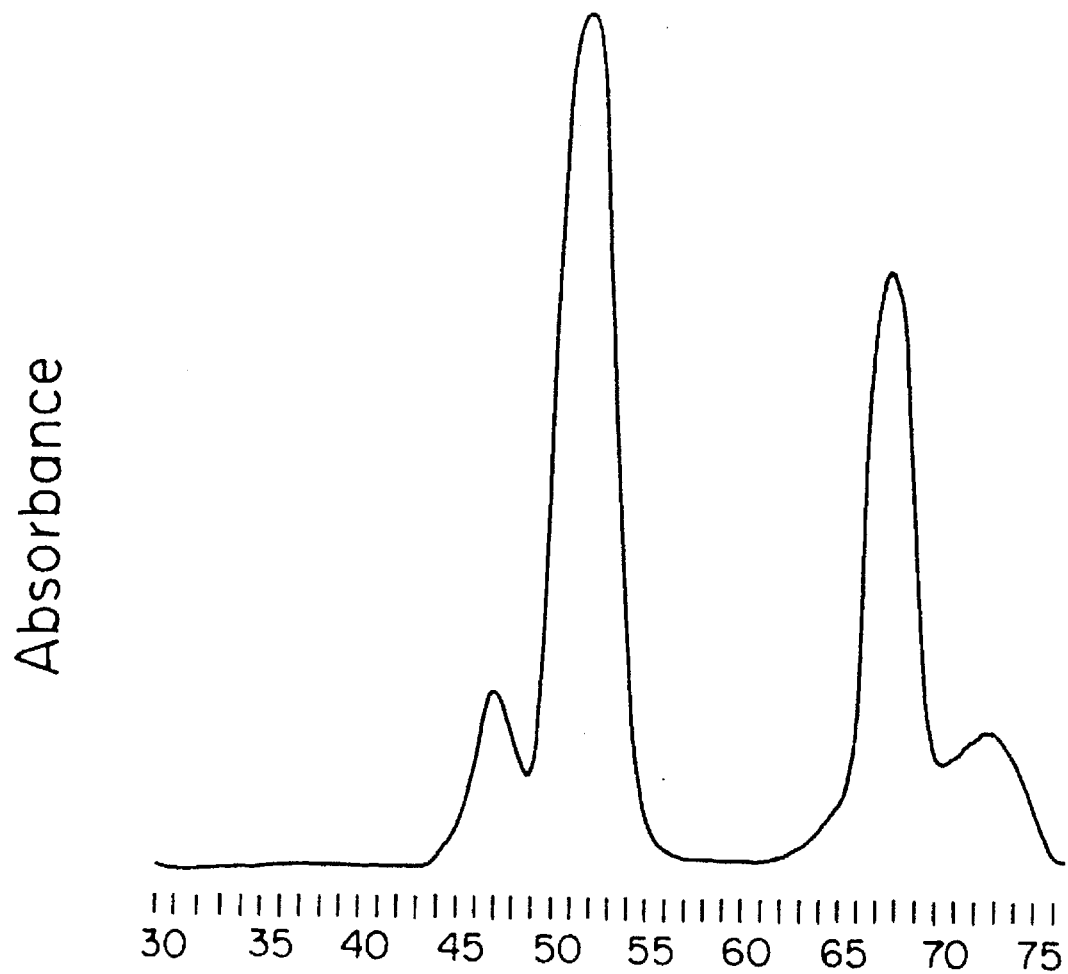
FIGS. 9A through C illustrate the purification of chiBR96-immunotoxin conjugates. BR96 and BD2 were chemically conjugated via a hindered disulfide linkage and purified by a two-step chromatography process.
Figure 9B:
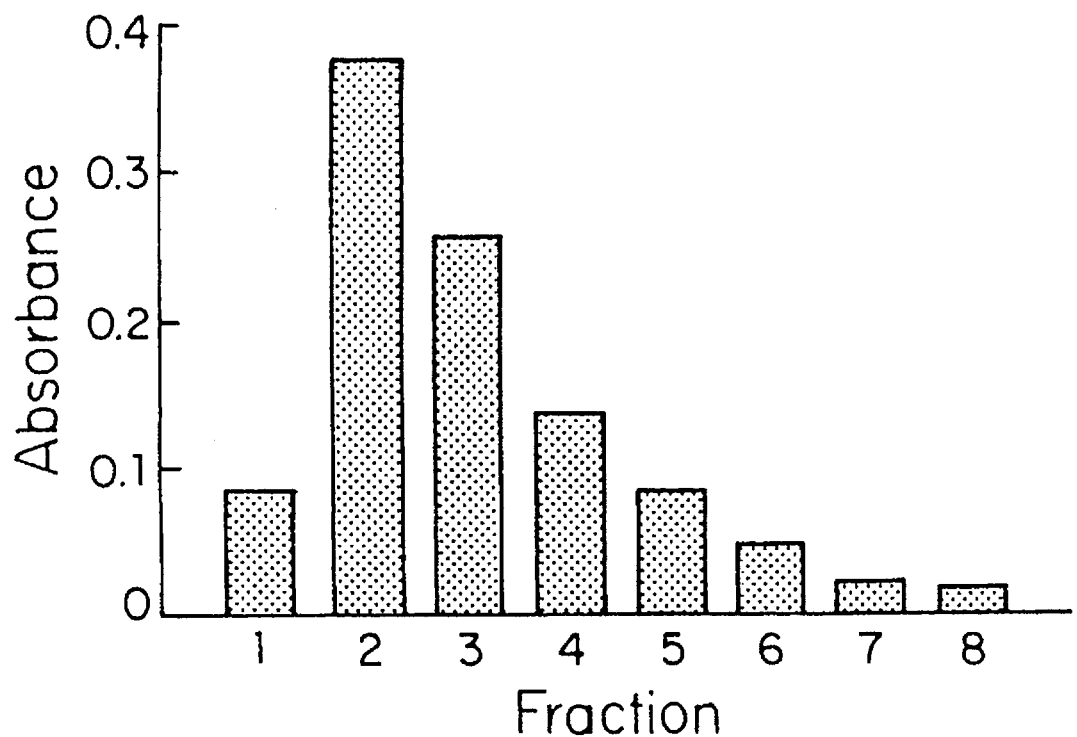
Figure 9C:
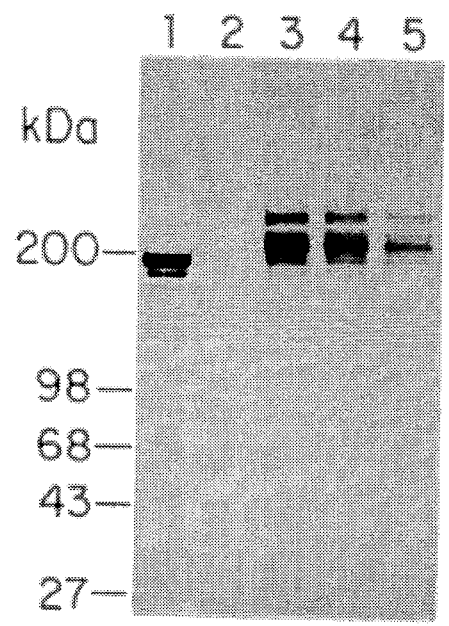

Immunotoxin conjugates were applied to a TSK-3000 size-exclusion column and separated from free toxin. The immunotoxin having a molecular weight of about 180 kDa and free antibody having a molecular weight of about 150 kDa eluted together and were further purified by chromatography on Blue-SEPHAROSE (Pharmacia) (FIG. 9A). Prior to adsorption to the Blue-SEPHAROSE, the partially purified immunotoxin sample was dialyzed into 0.1M sodium phosphate, pH 7.0. The Blue-SEPHAROS was equilibrated with the same buffer and the dialyzed immunotoxin sample was batch adsorbed to the Blue-SEPHAROSE (5 ml resin/5 mg immunotoxin) for 16 hours at 4° C. The mixture of Blue-SEPHAROSE and immunotoxin sample was packed into a 5 ml Econo column (Bio-Rad, Richmond, Calif.) and 1 ml fractions were collected as the column was eluted with a two-step gradient of increasing NaCL concentrations in 0.1M sodium phosphate, pH 7.0. The two steps of the gradient were 400 mM NaCl followed by 800 mM NaCl (FIG. 9B). Quantitation of the amount of immunotoxin in each fraction was determined at $OD_{280}$ and analyzed by non-reducing SDS-PAGE analysis (FIG. 9C).

Figure 10:
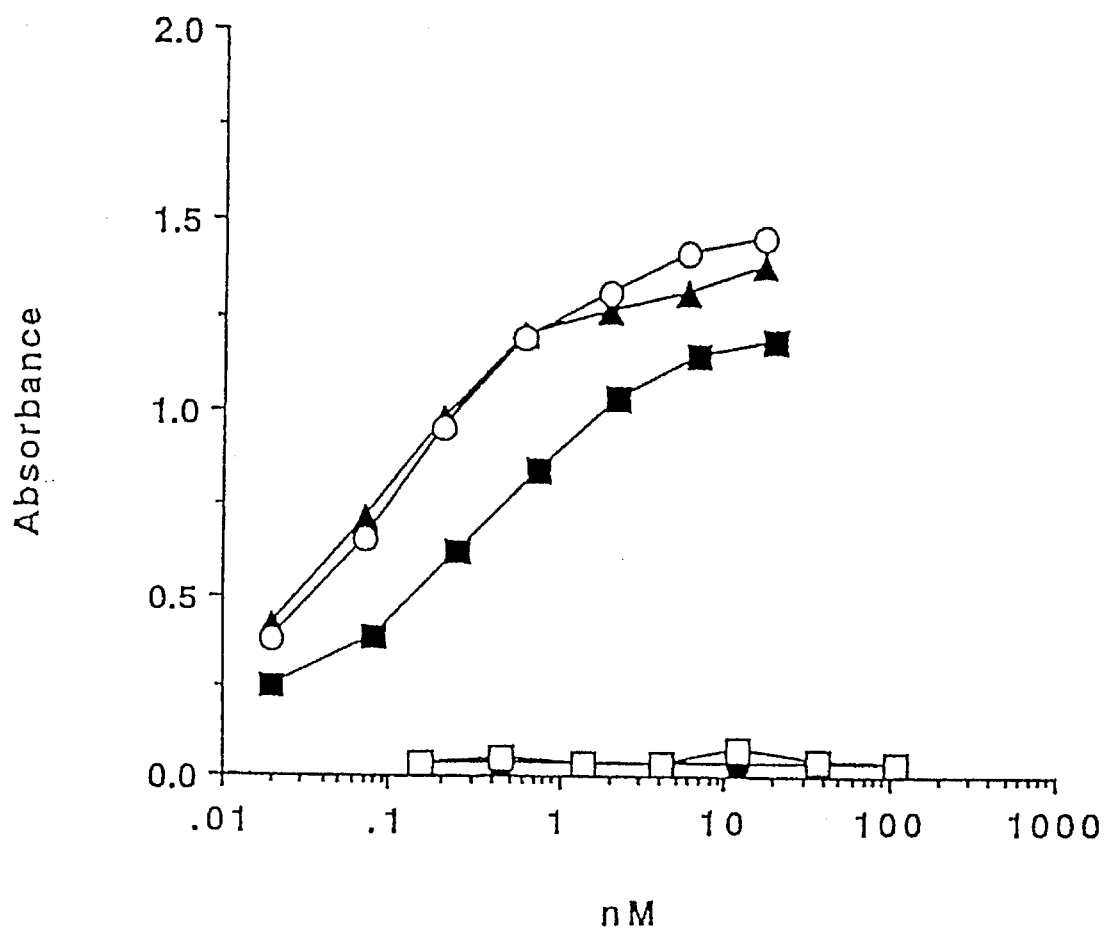
FIG. 10 illustrates the binding activity of BR96-BD2 and BR96-BD 1 immunotoxin conjugates. Binding of BR96-immunotoxins was determined using H3396 cell membranes. Specific antigen binding was detected with goat anti-human IgG horseradish peroxidase. Data represents duplicate data points. Chimeric BR96 (chiBR96, ■), chiBR96-BD2 (○), chiBR96-BD 1 (△), BD2 (□), BD 1 (●).

Antigen binding activity of chiBR96-BD2 and chiBR96-BD1 immunotoxin conjugates was determined by measuring the binding of the immunotoxin conjugates to isolated membranes of the human breast carcinoma cell line H3396. Both chiBR96-BD2 and chiBR96-BD1 conjugates were found to bind antigen on H3396 membrane similarly. The conjugate may bind slightly better than unconjugated BR96 antibody (FIG. 10), the increased binding possibly being due to the presence of antibody aggregates formed during the conjugation procedure. It has previously been shown that increased binding activity has been associated with dimers of BR96 (Wolff et al., 1993, *Cancer Res.* 53:2560). Both BD2 and BD1 unconjugated to antibody show no detectable binding to H3396 membranes (FIG. 10).

Membranes used for binding studies were from H3396 cells prepared by centrifuging $5 \times 10^7$ cells at 1500×g for five minutes and frozen at −70° C. The cell pellet was thawed at room temperature and lysed in 10 mM Tris-HCl, pH 7.4, 5 mM EDTA, 0.5 mM phenylmethyl sulfonylfluoride (PMSF) at 4° C. for 15 minutes, and homogenized. The lysed cells were centrifuged at 1500×g at 4° C. for 5 minutes to clarify the supernatant. The supernatant was further centrifuged at 7500×g at 4° C. for 80 minutes and the pellet was resuspended in PBS, 0.5 mM PMSF, 25 mM iodoacetamide. Membranes were collected by centrifuging the solution at 7500×g at 4° C. for 80 minutes and the pellet resuspended in PBS, 0.5 mM PMSF, 25 mM iodoacetamide, and the protein concentration determined by absorbence of $A_{280}$.

Assay of binding to the membrane was carried out by coating the surface of Iratoulon II 96 well plates (Dynatech Labs, Chantilly, Va.) with 10 μg/ml H3396 membranes in 0.1M sodium carbonated sodium bicarbonate buffer, pH 9.6, for 16 hours at 4° C. The plates were blocked with specimen diluent (Genetic Systems Corp., Seattle, Wash.) for one hour at room temperature and incubated with immunotoxin at 4° C. for 16 hours. Plates were washed with PBS three times followed by the addition of goat anti-human (heavy and light chains) horseradish peroxidase (American Qualex, La Mirada, Calif.) at 1:1000 in conjugate diluent (Genetic Systems Corp.). After incubation for one hour at room temperature, plates were washed five times with PBS, and developed with tetramethyl benzedine chromagen (Genetic Systems Corp.) for 10 minutes. The reaction was stopped with 1.3M $H_2SO_4$ and immunostaining was quantitated using a Bio-Tek microplate reader (Winooski, Vt.) at 450–630 nm.

Cytotoxicity of the chiBR96-BD2 immunotoxin was determined by plating H3396 tumor cells onto 96-well flat bottomed tissue culture plates ($1 \times 10^4$ cells/well) and kept at 37° C. for 16 hours. Dilutions of immunotoxin or immunotoxin components were made in culture media (IMDM, 10% FBS, 1% Penicillin/streptomycin) and 0.1 ml added to each well for 96 hours at 37° C. Each dilution was done in triplicate. After incubation with the immunotoxin, or toxin components, the wells were washed twice with PBS and 200 μl/well of 1.5 μM calcein-AM (Molecular Probes, Inc., Eugene, Oreg.) was added for 40 minutes at room temperature. Following incubation with calcein-AM, the amount of fluorescence was determined using a Fluorescence Concentration Analyzer (Baxter Healthcare Corp., Mundelein, Ill.) at excitation/emission wavelengths of 485 nm/530 nm. The data are presented as percent cell killing for each treatment calculated as:

$$100 - \left[ \frac{\text{(sample signal - background signal)}}{\text{(maximal signal - background signal)}} \times 100 \right]$$

Background signal was measured from cells treated with Triton X-100 and maximal signal was measured from non-immunotoxin treated cells.

Figure 11A:
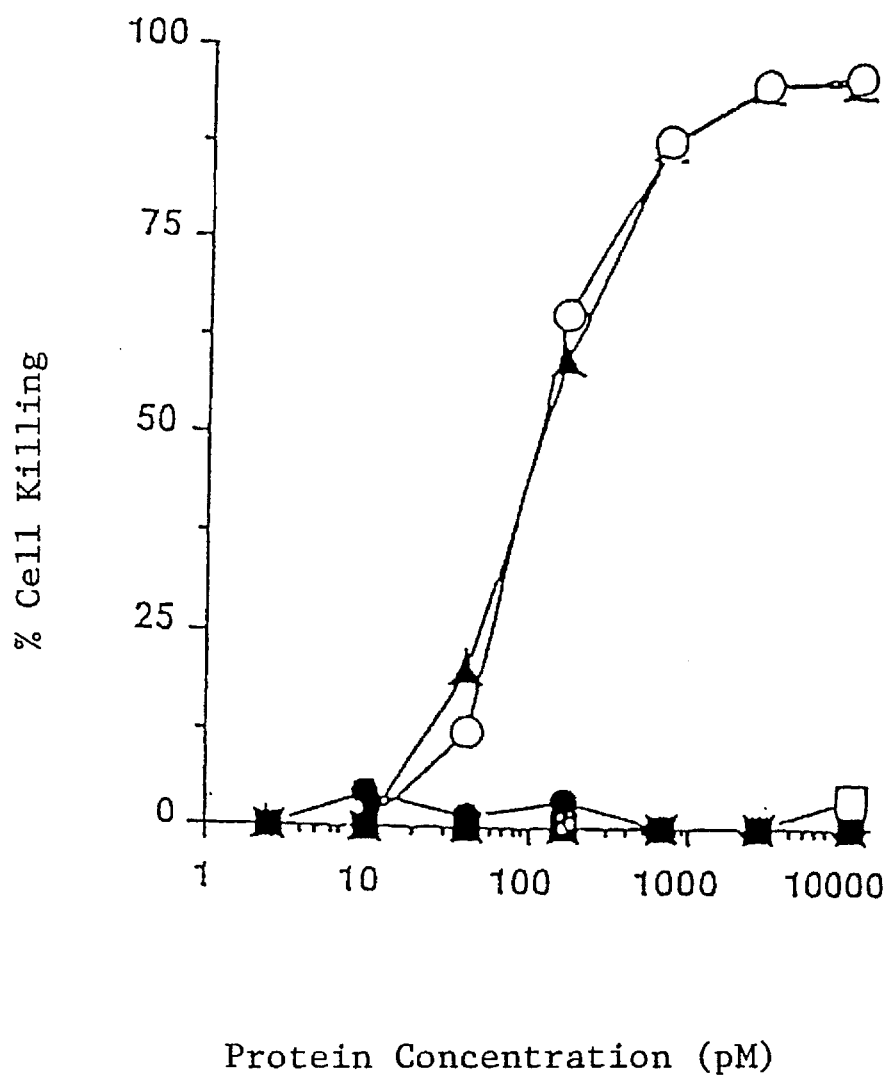
FIGS. 11A and 11B illustrate the cytotoxicity of chiBR96-BD2 and chiBR96-BD1 immunotoxin conjugates. Cell killing was determined following incubation of chiBR96-BD2 and chiBR96-BD 1 immunotoxin conjugates with (A) H3396 breast carcinoma cells (antigen positive) and (B) H3719 colon carcinoma cells (antigen negative) for 96 hours. Cell killing was determined by measuring calcein-AM hydrolysis into fluorescent calcein. ChiBR96, (■), chiBR96-BD2 (□), chiBR96-BD1 (▲), BD2 (□), BD 1(●).
Figure 11B:
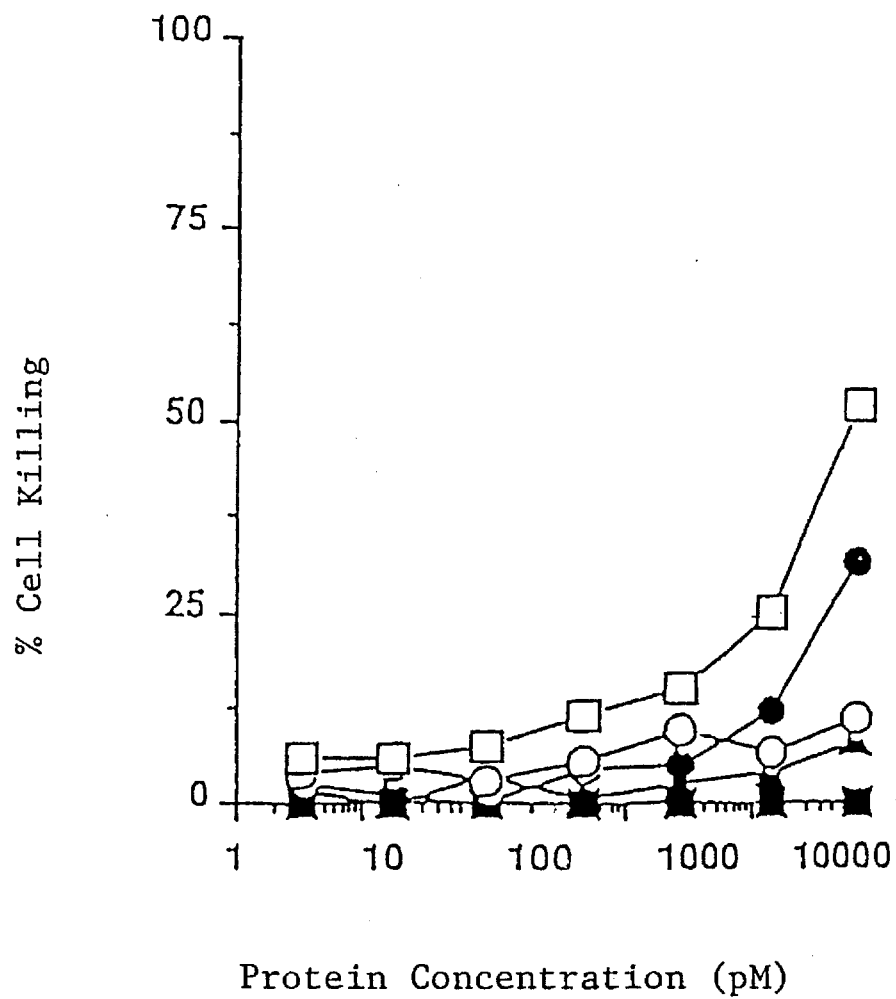

Cell killing activity of chiBR96-BD2 and chiBR96-BD1 immunotoxin conjugates were found to be cytotoxic to H3396 cells at a similar level with an $EC_{50}=100$ pM (FIG. 11A). H3719 colon carcinoma cells which express undetectable levels of BR96 antigen were found to be relatively insensitive to both chiBR96-BD2 and chiBR96-BD1 ($EC_{50} > 5 \times 10^4$ pM, FIG. 11B).

Protein synthesis inhibition activity was determined by measuring [3H]-leucine incorporation into cellular proteins following a 20-hour incubation of immunotoxin with H3396 cells and a four-hour pulse with [3H]-leucine. The immunotoxins chiBR96-BD2 and chiBR96-BD1 were added to H3396 cells ($1 \times 10^4$ cells/well) in a 96-well microtiter plate. The cells were grown to 75% confluence in IMDM medium with 10% FBS. The cells were incubated with the test material for a total of 24 hours, the last four hours with 1 μCi of [3H]-leucine added to each well. The cells were lysed by freeze-thawing and harvested using a TomTec Cell Harvester (TomTec Inc., Orange, Conn.). Incorporation of [3H]-leucine into cellular protein was determined by an LKB Beta-Plate Liquid Scintillation Counter.

EXAMPLE 9

Cloning of Bryodin 2 from the Leaves of *Bryonia dioica*

In this example, degenerate oligonucleotide probes were used to isolate a small region of DNA, amplified from *Bryonia dioica* mRNA, that corresponded to an amino acid sequence of Bryodin 2. These regions of DNA were sequenced and a series of oligonucleotide primers exactly corresponding to the determined DNA sequence were designed and, together with degenerate primers designed from the amino acid sequence of internal peptide fragments of BD2, were used to amplify a longer stretch of DNA encoding BD2. Having successfully isolated and sequenced a substantial portion of BD2 DNA, 5' and 3' RACE techniques were used to identify the exact 5' and 3' ends of the cDNA sequence encoding the entire Bryodin 2 open reading frame.

Briefly, total RNA was extracted from *Bryonia dioica* leaf material by finely grinding leaves in dry ice and homogenizing in TRI Reagent (phenol, guanidine thiocyanate, Molecular Research Center, Inc., Cincinnati, Ohio) at 10 ml/g tissue. RNA was extracted with chloroform, precipitated with isopropanol, washed with 75% ethanol and dissolved in DEPC (diethyl pyrocarbonate) treated water. Total RNA was quantitated and analyzed by electrophoresis in formaldehyde-agarose gels and visualized by staining with ethidium bromide.

First strand cDNA was synthesized by incubating 1 μg total *B. dioica* leaf RNA template and 10 pmole oligo(dT)-primer XSCT17 (Table 3) at 65° C for 10 min. and then on ice for 2 min. to allow annealing to occur. This was followed by adding synthesis buffer (20 mM Tris-HCl, pH 8.3, 50 mM KCl,2.5 mM MgCl), 10 mM dNTP mix (5 μM final concentration), 10 mM dithiotreitol and 200 U Superscript reverse transcriptase to the RNA mixture and incubating for 30 min. at 42° C. RNAse H (2 U) was then added and the mixture was incubated for an additional 10 min. The cDNA synthesized in this reaction was PCR amplified using two sets of degenerate oligonucleotides (a) BD2 p 14 (128-fold degeneracy) and BD2 p19, and (b) BD2 p18 (512-fold degeneracy) and BD2 p19 (See Table 3) at 25 pmole each. An approximately 500 base pair single band was obtained using primer set (b) after separation of the cDNA by agarose gel electrophoresis and visualization with ethidium bromide.

The products of the PCR reaction were subcloned into the vector pCRII (Invitrogen Corp.) using the TA cloning kit. Briefly, PCR product was combined with ligation buffer, pCRII vector (50 ng) and 4 U T4 DNA ligase at 1:1, 1:3 and 1:5 vector to insert ratios. The reactions were incubated overnight at 16° C. DH5α *E. coli* were transformed with 3 μl of the ligation reaction mixture by incubation on ice for 30 min., followed by a 42° C. incubation for 45 sec., 2 min. on ice, and an incubation at 37° C. in 450 μl of SOC (20 mM glucose, 10 mM $MgSO_4$, 10 mM $MgCl_2$, 2% tryptone, 0.5% yeast extract, 10 mMNaCl, 2.5 mM KCl) for 1 hr. Cells were plated on LB agar plates containing ampicillin (50 μg/ml), 25 μl X-Gal (40 mg/ml in dimethyl formamide) and 25 μl isopropyl 1-thio-β-D-galactopyranoside (IPTG, 240 mg/ml) and incubated overnight at 37° C.

PCR analysis of recombinant clones was carried out using Universal M13 forward and reverse primers (Table 3) followed by visualization by agarose gel electrophoresis. Briefly, positive clones were incubated at 37° C. in 50 μl of LB broth containing 50 μl/ml ampicillin for 1 hr. Cells (12 μl ) were diluted in 50 μl of 10 mM Tris-HCl and 1 mM EDTA and incubated at 95° C. for 5 min. The PCR reaction (100 μl) consisted of 1× PCR buffer (10 mM Tris-HCl, pH 8.3, 50 mM KCl, 1.5 mM $MgCl_2$), dNTP mix (200 μM), 25 pmole each M13 forward and M13 reverse primers, 10 μl cells (test DNA) and 2.5 U Taq DNA polymerase. Thirty-five cycles were run using a GeneAmp PCR System Model 9600 (Perkin Elmer Cetus) using the cycle conditions of 94° C. for 3 min., 94° C. 15 sec., 55° C. 15 sec., 72° C. 1.15 min.×35; 72° C. 6 min. and hold at 4° C. Reaction visualized by agarose gel electrophoresis. Clones were selected for DNA sequencing analysis based on the presence of a 500+ bp insert.

DNA was sequenced by dideoxynucleotide termination using Sequenase (United States Biochemical). Four separate clones containing a nucleotide sequence determined to encode the previously determined amino-terminal amino acid sequence of BD2 were identified. A 468 bp cDNA fragment which corresponded to the majority of the BD2 amino acid sequence was used as template for 3' and 5'

TABLE 3

| BD2 Oligonucleotides Used for Cloning | |
|---|---|
| BD2p14 | 5'-ACN TAC(T) AAA(G) ACN TTC(T) AT-3' |
| (SEQ ID NO: 16) | 5' oligo, (14–20 aa) TYKTFI 128-fold |
| BD2P18 | 5'-GGN GCN ACN TAT AAA(G) ACN AT-3' |
| (SEQ ID NO: 17) | 5' oligo (12–20 aa) GATYKTFI 512-fold |
| BD2p19 | 5'-CTC A(G)AT ATA C(T)TT A(G)AA T(C)CT CGC AGC CTC-3' |
| (SEQ ID NO: 18) | 3' oligo (163–169 aa) EAARFKYI |
| XSCT17 | 5'-GAC TCG AGT CGA CAT CGA TTTTTTTTTTTTTTTTT-3' |
| (SEQ ID NO: 19) | 3' oligo |
| XSC | 5'-GAC TCG AGT CGA CAT CG-3' |
| (SEQ ID NO: 20) | 3' oligo |
| BD2 3'RACE #2 | 5'-ACC ACA CTC ACG GTT GGA ACT CCA-3' |
| (SEQ ID NO: 21) | 5' oligo (24–31 aa) TKLTVGTP |
| BD2 5'RACE #4 | 5'-TGG ACT TCC AAC CGT GAG TGT GGT-3' |
| (SEQ ID NO: 22) | 3' oligo (24–31 aa) TKLTVGTP |
| BD2 5'RACE #5 | 5'-C GTT CAC TAC ATC TTA AGC CAC AGT GAC-3' |
| (SEQ ID NO: 23) | 3' oligo (62–71 aa) VTVALDVVNV |
| BD2-3'RACE #11 | 5'-GA CTT CCT TAT GGA GGG AAT TAC GAT GGC CTT-3' |
| (SEQ ID NO: 24) | 3' oligo, (104–114 aa) RLPYGGNYDGL |
| 5'RACE AP | 5'-GGC CAC GCG TCG ACT AGT ACG GGI IGG GII GGG IIG-3' |
| (SEQ ID NO: 25) | |
| M13 Reverse Primer | 5'-CAG GAA ACA GCT ATG AC-3' |
| (SEQ ID NO: 26) | |
| M13 Forward Primer | 5'-CTG GCC GTC GTT TTA C-3' |
| (SEQ ID NO: 27) | |

RACE techniques, which were used to identify the start codon, to confirm the amino terminus of the BD2 gene, and to obtain DNA sequence to the polyA tail.

Amplification by 3' RACE was carried out by using a 3' RACE System (Gibco BRL). Briefly, 0.5 µg total BD leafRNA was incubated with 10 pmole oligonucleotide primer XSC-T17 (Table 3) at 65° C. for 1 min. followed by 2 min. on ice. The RNA mixture was then mixed and incubated at 42° C. for 2 min. with synthesis buffer (20 mM Tris-HC1, pH 8.4, 50 mM KCl, 2.5 mM MgCl$_2$, 100 µg/ml BSA), dNTP mix (500 µM each), and 2 µl 0.1M DTT before the addition of 200 units Superscript reverse transcriptase and a further incubation at 42° C. for 30 min. The 3' end of BD2 cDNA was PCR amplified with 25 pmoles each of primers BD2 3' RACE #2 and XSC (Table 3) in synthesis buffer with 200 µM dNTP mix and 2.5 U Taq polymerase. An 800+ bp band was visualized by agarose gel electrophoresis and was cloned into the TA cloning vector pCRII as described previously. Clones containing BD2 sequences were selected by hybridization of colonies lifted onto nylon membranes, as described below, probed with [$^{32}$P]-labeled BD2-3' RACE #11.

After incubation, the agar plates were cooled at 4° C. for 2 hr after which colonies were lifted onto nylon membranes for 1 min. The membranes were incubated in 1.5M NaCl, 0.5M NaOH to denature the DNA followed by neutralization in 1.5M NaCl,0.5M Tris-HCl, pH 7.2, and 0.1 mM EDTA. The membranes were then washed in 2× SSC and the DNA was crosslinked to the membranes in a UV Stratalinker 1800 (Stratagene). Prehybridization was carried out by incubating the membranes in 6×SSC, 5×Denhardt's, 0.05% sodium pyranophosphate, 0.5% SDS and 0.02 mg/ml salmon testes DNA at 50° C. overnight. Hybridization was carried out with the radiolabeled probe [$^{32}$P] BD2 RACE #11 (0.5–2×10$^6$ cpm/ml) in 6× SSC, 1× Denhardt's, 0.05% sodium pyranophosphate, and 100 µg/ml yeast RNA at 50° C. for 4 hr. The membranes were washed with 6× SSC, 0.1% sodium pyranophosphate at 37° C., followed by exposure to autoradiograph film. Miniplasmid DNA was made from the positive white colonies and analyzed by PCR and DNA sequencing.

5' RACE was performed using the 5' RACE System (Gibco BRL) as per manufacturer's instructions. Briefly, 1 µg of BD leaf total RNA and 2 pmole primer BD2 5' RACE #5 were combined and denatured at 70° C. for 9 min. followed by incubation at 42° C. for 30 min. in synthesis buffer 0.01M DTT, dNTP mix (500 µM each) and 200 U Superscript reverse transcriptase in a total volume of 19 µl. The RNA template was degraded with 2 U RNase H at 55° C. for 10 min. cDNA was purified with a Glassmax spin cartridge to remove primers, unincorporated dNTPs and proteins by adding 95 µl of binding buffer (6M sodium iodide) to the reaction mix and transferring the reaction contents to a Glassmax spin cartridge. The loaded cartridge was centrifuged at 13,000 xg for 1 min. and then washed three times in 1× Glassmax wash buffer and once in 70% ethanol. The cDNA was eluted with 50 µl of water (65° C.). Purified cDNA was dC-tailed by denaturing 10 µl of cDNA at 70° C. for 6 min. This was followed by incubation in 1×synthesis buffer with 2 mM dCTP (200 µM) and 10 U TdT in a total volume of 20 µl at 37° C. for 10 min. and then incubating the mixture at 65° C. for 15 min.

The dC-tailed cDNA (5 µl) was PCR amplified using 25 pmole each of BD2 5' RACE #4 and 5' RACE AP (Table 3) for 35 cycles as described previously above. DNA was analyzed by agarose gel electrophoresis which revealed various 100–200 bp fragments which were subcloned into pCRII as described previously. PCR analysis of white colonies using Universal M13 forward and M13 reverse primers identified clones containing inserts. Two positive clones were selected for DNA sequencing and extended the DNA sequence for BD2 63 bp upstream from the beginning sequences of the mature BD2 protein. The natural initiating methionine and the putative signal sequence were identified. Clone pSE20.0 has been deposited with the American Type Culture Collection, 12301 Parklawn Drive, Rockville Md. 20852 on Oct. 19, 1994 and designated ATCC 75917 which contains the plasmid having the oligonucleotide sequence as depicted in FIG. 13.

We claim:

1. A ribosome-inactivating protein comprising a single chain protein having a molecular weight of about 27,000 daltons by polyacrylamide gel electrophoresis under reducing and non-reducing conditions, an $EC_{50}$ of about 0.017 mM in a rabbit reticulocyte lysate system, an $LD_{50}$ in mice of greater than 10 mg/kg when administered intravenously and about 8 mg/kg when administered intraperitoneally, and further comprising an amino terminal amino acid residue sequence comprises the following contiguous amino acid sequence:

Val Asp Ile Asn Phe Ser Leu Ile Gly Ala Thr Gly Ala Thr Tyr Lys Thr Phe Ile Arg Asn Leu Arg Thr Thr Leu Thr Val Gly Thr Pro Arg (SEQ ID #1), and (a) Leu Pro Tyr Gly Gly Ass Tyr Asp Gly Leu Glu Thr Ala Ala Gly Arg (SEQ ID #2);

Glu Asn Ile Glu Leu Gly Phe Ser Glu Ile Ser Ser Ala Ile Gly Asn Met Phe Arg (SEQ ID #3);

(c) Phe Arg His Asn Pro Gly Thr Ser Val Pro Arg Ala Phe Ile Val Ile Ile Gln Thr Val Ser Glu Ala Ala Arg Phe Lys Tyr Ile Glu Gln Arg (SEQ ID #4):

(d) Tyr Ile Glu Gln Arg Val Ser Glu Asn Val Gly Thr Lys (SEQ ID #5);

(e) Phe Lys Pro Asp Pro Ala Phe Leu Ser Leu Gln Asn Ala Trp Gly Ser Leu Ser Glu Gln Ile Gln Ile Ala Gln Thr Arg Gly Gly Glu Phe Ala Arg Pro Val Glu Leu Arg Thr (SEQ ID #6); or (f) Leu Arg Thr Val Ser Asn Thr Pro Thr Phe Val Thr Asn Val Asn (SEQ ID #7), as determined by automated amino acid sequencing.

2. A composition comprising the ribosome-inactivating protein of claim 1 linked to a ligand to form a toxin-ligand conjugate.

3. The composition of claim 2, wherein the ligand comprises an immunoglobulin, adhesion molecule, or a polypeptide, peptide or non-peptide ligand.

4. The composition of claim 3, wherein the ligand is selected from the group consisting of transferrin, an epidermal growth factor, bombesin, gastrin, gastrin-releasing peptide platelet-derived growth factor, interleukin-2, interleukin-6, transforming growth factors, steroid, carbohydrate and lectin.

5. The composition of claim 3, wherein the ligand is an immunoglobulin.

6. The composition of claim 5, wherein the immunoglobulin is an antigen recognizing fragment, a chimeric antibody, a bifunctional antibody or a hybrid antibody.

7. The composition of claim 6, wherein the antigen-recognizing fragment is a Fab', (Fab')$_2$, Fv or Fab fragment.

8. The composition of claim 6, wherein the immunoglobulin is immunospecific for a Lewis Y-related antigen and is internalized by carcinoma cells.

9. The composition of claim 6, wherein the chimeric immunoglobulin is chimeric BR96 as produced by the hybridoma deposited with the American Type Culture Collection and designated ATCC HB 10460.

10. A pharmaceutical composition comprising the ribosome-inactivating protein of claim 1 and a pharmaceutically acceptable carrier or adjuvant.

11. The pharmaceutical composition of claim 10, wherein the pharmaceutically acceptable carrier or adjuvant is human serum albumin, albumin, an ion exchanger, alumina, lecithin, a buffer substance, salt or electrolyte.

12. A pharmaceutical composition comprising an immunotoxin comprising bryodin 2 and a ligand, and a pharmaceutically acceptable carrier or adjuvant.

13. The pharmaceutical composition of claim 12, wherein the ligand is an immunoglobulin.

14. The pharmaceutical composition of claim 13, wherein the immunoglobulin is an antigen recognizing fragment, a chimeric antibody, a bifunctional antibody or a hybrid antibody.

15. The composition of claim 14, wherein the immunoglobulin is a chimeric antibody.

16. The composition of claim 15, wherein the chimeric antibody is chimeric BR96 as produced by the hybridoma deposited with the American Type Culture Collection and designated ATCC HB 10460.

17. An isolated oligonucleotide sequence encoding a ribosome-inactivating protein from *Bryonia dioica* the protein comprising the amino acid sequence of Sequence ID NO: 15, or a complement of the isolated oligonucleotide sequence.

18. The isolated oligonucleotide sequence of claim 17 comprising the nucleotide sequence of Sequence ID NO: 14 from about nucleotide number 28 to about nucleotide number 873.

19. The isolated oligonucleotide sequence of claim 17 comprising the nucleotide sequence of Sequence ID NO: #14 from about nucleotide number 91 to about nucleotide number 873.

20. The isolated nucleotide sequence of claim 17, wherein the nucleotide sequence encodes a biologically active fragment of bryodin 2 which inhibits protein synthesis in vitro.

21. A recombinant vector comprising an oligonucleotide sequence encoding a ribosome-inactivating protein from *Bryodin dioica*, the protein comprising the amino acid sequence of Sequence ID NO: 15.

22. The recombinant vector of claim 21, further comprising transcriptional and translational control sequences operably linked to the oligonucleotide sequence encoding the ribosome-inactivating protein.

23. The recombinant vector of claim 21 wherein the vector is pSE20.0 as deposited with the American Type Culture Collection and designated ATCC 95917.

24. A host cell transfected with a recombinant vector of claim 21.

25. A host cell transfected with a recombinant vector of claim 23.

26. A method for the recombinant expression of bryodin 2 comprising transfecting a host cell with an expression vector comprising an oligonucleotide sequence encoding the contiguous amino acid sequence of Sequence ID NO: 15, growing the transfected host cells, inducing the transfected host cells to express recombinant bryodin 2 and isolating the expressed recombinant bryodin 2.

27. The method of claim 26, wherein the host cell is a bacteria, a plant cell, a yeast or a mammalian cell.

28. A method for producing a recombinant bryodin 2-ligand fusion protein comprising a transfected host cell with an expression vector comprising an oligonucleotide sequence encoding the contiguous amino acid sequence of Sequence ID NO: 2 from about amino acid residue 22 to about amino acid residue 282 operatively linked with an oligonucleotide sequence which encodes a ligand, growing the transfected host cells, inducing the transfected host cells to express the recombinant bryodin 2-ligand fusion protein, and isolating the expressed recombinant fusion protein.

29. The method of claim 28, wherein the host cell is a bacteria, a plant, a yeast or a mammalian cell.

30. The method of claim 29, wherein the ligand is a large molecular weight protein, a small molecular weight protein, a polypeptide, or a peptide-ligand.

31. The method of claim 30, wherein the ligand is an immunoreactive ligand.

32. The method of claim 31, wherein the immunoreactive ligand is an antigen recognizing immunoglobulin, or an antigen-recognizing fragment thereof, a chimeric antibody, a bifunctional antibody, a hybrid antibody or a single chain antibody.

33. The method of claim 32, wherein the antigen recognizing fragment is a Fab', F(ab')$_2$, Fv or Fab fragment of an immunoglobulin.

34. A method for killing a target cell comprising contacting the target cell with an effective amount of a toxin-ligand conjugate of claim 2, wherein the ligand specifically binds to or reactively associates with a receptor moiety on the surface of the target cell, for a time sufficient to kill the target cell.

35. The method of claim 34, wherein the ligand comprises an immunoglobulin, adhesion molecule, or a polypeptide, peptide or nonpeptidyl ligand.

36. The method of claim 34, wherein the immunoglobulin is an antigen binding fragment, a chimeric antibody, a bifunctional antibody or a hybrid antibody.

37. The method of claim 36, wherein the chimeric immunoglobulin is chimeric BR96 as produced by the hybridoma deposited with the American Type Culture Collection and designated ATCC HB 10460.

38. A method for inhibiting the proliferation mammalian tumor cells comprising contacting the mammalian tumor cells with a proliferation inhibiting amount of a toxin-ligand conjugate of claim 5, wherein the tumor targeted toxin is joined to a ligand specific for a tumor-associated antigen so as to inhibit proliferation of the mammalian tumor cells.

39. The method of claim 38, wherein the ligand comprises an immunoglobulin, adhesion molecule, or a polypeptide, peptide or nonpeptidyl ligand.

40. The method of claim 38, wherein the immunoglobulin is an antigen binding fragment, a chimeric antibody, a bifunctional antibody or a hybrid antibody.

41. The method of claim 40, wherein the chimeric immunoglobulin is chimeric BR96 as produced by the hybridoma deposited with the American Type Culture Collection and designated ATCC HB10460.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 32 amino acids
( B ) TYPE: amino acid
( D ) TOPOLOGY: linear ( i i ) MOLECULE TYPE: peptide ( v ) FRAGMENT TYPE: N-terminal ( v i ) ORIGINAL SOURCE:
( A ) ORGANISM: Bryonica dioica
( F ) TISSUE TYPE: Root ( x i ) SEQUENCE DESCRIPTION: SEQ ID NO:1:

```
Val  Asp  Ile  Asn  Phe  Ser  Leu  Ile  Gly  Ala  Thr  Gly  Ala  Thr  Tyr  Lys
 1              5                        10                       15

Thr  Phe  Ile  Arg  Asn  Leu  Arg  Thr  Thr  Leu  Thr  Val  Gly  Thr  Pro  Arg
```

20                              25                              30

(2) INFORMATION FOR SEQ ID NO:2:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Bryonica dioica
        (F) TISSUE TYPE: Root (xi) SEQUENCE DESCRIPTION: SEQ ID NO:2:

Leu  Pro  Tyr  Gly  Gly  Asn  Tyr  Asp  Gly  Leu  Glu  Thr  Ala  Ala  Gly  Arg
    1                   5                        10                       15

(2) INFORMATION FOR SEQ ID NO:3:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Bryonica dioica
        (F) TISSUE TYPE: Root (xi) SEQUENCE DESCRIPTION: SEQ ID NO:3:

Glu  Asn  Ile  Glu  Leu  Gly  Phe  Ser  Glu  Ile  Ser  Ser  Ala  Ile  Gly  Asn
    1                   5                        10                       15

Met  Phe  Arg (2) INFORMATION FOR SEQ ID NO:4:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Bryonica dioica
        (F) TISSUE TYPE: root (xi) SEQUENCE DESCRIPTION: SEQ ID NO:4:

Phe  Arg  His  Asn  Pro  Gly  Thr  Ser  Val  Pro  Arg  Ala  Phe  Ile  Val  Ile
    1                   5                        10                       15

Ile  Gln  Thr  Val  Ser  Glu  Ala  Ala  Arg  Phe  Lys  Tyr  Ile  Glu  Gln  Arg
                        20                       25                       30

(2) INFORMATION FOR SEQ ID NO:5:

(i) SEQUENCE CHARACTERISTICS:
        (A) LENGTH: 13 amino acids
        (B) TYPE: amino acid
        (D) TOPOLOGY: linear (ii) MOLECULE TYPE: peptide ( v ) FRAGMENT TYPE: internal ( v i ) ORIGINAL SOURCE:
    ( A ) ORGANISM: Bryonica dioica
    ( F ) TISSUE TYPE: root ( x i ) SEQUENCE DESCRIPTION: SEQ ID NO:5:

```
Tyr Ile Glu Gln Arg Val Ser Glu Asn Val Gly Thr Lys
1               5                   10
```

( 2 ) INFORMATION FOR SEQ ID NO:6:

( i ) SEQUENCE CHARACTERISTICS:
    ( A ) LENGTH: 39 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: Bryonica dioica
    ( F ) TISSUE TYPE: root ( x i ) SEQUENCE DESCRIPTION: SEQ ID NO:6:

```
Phe Lys Pro Asp Pro Ala Phe Leu Ser Leu Gln Asn Ala Trp Gly Ser
1               5                   10                  15

Leu Ser Glu Gln Ile Gln Ile Ala Gln Thr Arg Gly Gly Glu Phe Ala
            20                  25                  30

Arg Pro Val Glu Leu Arg Thr
            35
```

( 2 ) INFORMATION FOR SEQ ID NO:7:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( v i ) ORIGINAL SOURCE:
    ( A ) ORGANISM: Bryonica dioica
    ( F ) TISSUE TYPE: root ( x i ) SEQUENCE DESCRIPTION: SEQ ID NO:7:

```
Leu Arg Thr Val Ser Asn Thr Pro Thr Phe Val Thr Asn Val Asn
1               5                   10                  15
```

( 2 ) INFORMATION FOR SEQ ID NO:8:

( i ) SEQUENCE CHARACTERISTICS:
    ( A ) LENGTH: 43 amino acids
    ( B ) TYPE: amino acid
    ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Bryonia dioica
    ( F ) TISSUE TYPE: root ( x i ) SEQUENCE DESCRIPTION: SEQ ID NO:8:

```
Asp Val Ser Phe Arg Leu Ser Gly Ala Thr Thr Thr Ser Tyr Gly Val
1               5                   10                  15
```

```
        Phe   Ile   Lys   Asn   Leu   Arg   Glu   Ala   Leu   Pro   Tyr   Glu   Arg   Lys   Val   Tyr
                          20                        25                        30

Asn   Ile   Pro   Leu   Leu   Leu   Arg   His   Xaa   Ile   Gly
                          35                        40
```

( 2 ) INFORMATION FOR SEQ ID NO:9:

( i ) SEQUENCE CHARACTERISTICS:
    ( A ) LENGTH: 38 amino acids
    ( B ) TYPE: amino acid
    ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Ricinus communis ( x i ) SEQUENCE DESCRIPTION: SEQ ID NO:9:

```
        Ile   Phe   Pro   Lys   Gln   Tyr   Pro   Ile   Ile   Asn   Phe   Thr   Thr   Ala   Gly   Ala
        1                       5                         10                        15

Thr   Val   Gln   Ser   Tyr   Thr   Asn   Phe   Ile   Arg   Ala   Val   Arg   Gly   Arg   Leu
                          20                        25                        30

Thr   Thr   Gly   Ala   Asp   Val
                          35
```

( 2 ) INFORMATION FOR SEQ ID NO:10:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Momordia cochinchinensis ( x i ) SEQUENCE DESCRIPTION: SEQ ID NO:10:

```
        Asp   Val   Ser   Phe   Arg   Leu   Ser   Gly   Ala   Asp   Pro   Arg   Ser   Tyr   Gly   Met
        1                       5                         10                        15

Phe   Ile   Lys   Asp   Leu   Arg   Asn   Ala   Leu   Pro   Phe   Arg   Glu   Lys   Val
                          20                        25                        30
```

( 2 ) INFORMATION FOR SEQ ID NO:11:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Trichosanthes kirilowii ( x i ) SEQUENCE DESCRIPTION: SEQ ID NO:11:

```
        Asp   Val   Ser   Phe   Arg   Leu   Ser   Gly   Ala   Thr   Ser   Ser   Ser   Tyr   Gly   Val
        1                       5                         10                        15

Phe   Ile   Ser   Asn   Leu   Arg   Lys   Ala   Leu   Pro   Asn   Glu   Arg   Lys   Leu
                          20                        25                        30
```

( 2 ) INFORMATION FOR SEQ ID NO:12:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( v ) FRAGMENT TYPE: N-terminal ( v i ) ORIGINAL SOURCE:
    ( A ) ORGANISM: Luffa cyindrica ( x i ) SEQUENCE DESCRIPTION: SEQ ID NO:12:

| Asp | Val | Arg | Phe | Ser | Leu | Ser | Gly | Ser | Ser | Ser | Thr | Ser | Tyr | Ser | Lys |
|---|---|---|---|---|---|---|---|---|---|---|---|---|---|---|---|
| 1 | | | | 5 | | | | | 10 | | | | | 15 | |

| Phe | Ile | Gly | Asp | Leu | Arg | Lys | Ala | Leu | Pro | Ser | Asn | Gly | Thr | Val |
|---|---|---|---|---|---|---|---|---|---|---|---|---|---|---|
| | | | 20 | | | | | 25 | | | | | 30 | |

( 2 ) INFORMATION FOR SEQ ID NO:13:

( i ) SEQUENCE CHARACTERISTICS:
    ( A ) LENGTH: 286 amino acids
    ( B ) TYPE: amino acid
    ( D ) TOPOLOGY: linear ( i i ) MOLECULE TYPE: protein ( v ) FRAGMENT TYPE: N-terminal ( v i ) ORIGINAL SOURCE:
    ( A ) ORGANISM: Momordica charantia ( x i ) SEQUENCE DESCRIPTION: SEQ ID NO:13:

| Met | Val | Lys | Cys | Leu | Leu | Leu | Ser | Phe | Leu | Ile | Ile | Ala | Ile | Phe | Ile |
|---|---|---|---|---|---|---|---|---|---|---|---|---|---|---|---|
| 1 | | | | 5 | | | | | 10 | | | | | 15 | |

| Gly | Val | Pro | Thr | Ala | Lys | Gly | Asp | Val | Asn | Phe | Asp | Leu | Ser | Thr | Ala |
|---|---|---|---|---|---|---|---|---|---|---|---|---|---|---|---|
| | | | 20 | | | | | 25 | | | | | 30 | | |

| Thr | Ala | Lys | Thr | Tyr | Thr | Lys | Phe | Ile | Glu | Asp | Phe | Arg | Ala | Thr | Leu |
|---|---|---|---|---|---|---|---|---|---|---|---|---|---|---|---|
| | | 35 | | | | | 40 | | | | | 45 | | | |

| Pro | Phe | Ser | His | Lys | Val | Tyr | Asp | Ile | Pro | Leu | Leu | Tyr | Ser | Thr | Ile |
|---|---|---|---|---|---|---|---|---|---|---|---|---|---|---|---|
| | 50 | | | | | 55 | | | | | 60 | | | | |

| Ser | Asp | Ser | Arg | Arg | Phe | Ile | Leu | Leu | Asp | Leu | Thr | Ser | Tyr | Ala | Tyr |
|---|---|---|---|---|---|---|---|---|---|---|---|---|---|---|---|
| 65 | | | | | 70 | | | | | 75 | | | | | 80 |

| Glu | Thr | Ile | Ser | Val | Ala | Ile | Asp | Val | Thr | Asn | Val | Tyr | Val | Val | Ala |
|---|---|---|---|---|---|---|---|---|---|---|---|---|---|---|---|
| | | | | 85 | | | | | 90 | | | | | 95 | |

| Tyr | Arg | Thr | Arg | Asp | Val | Ser | Tyr | Phe | Phe | Lys | Glu | Ser | Pro | Pro | Glu |
|---|---|---|---|---|---|---|---|---|---|---|---|---|---|---|---|
| | | | 100 | | | | | 105 | | | | | 110 | | |

| Ala | Tyr | Asn | Ile | Leu | Phe | Lys | Gly | Thr | Arg | Lys | Ile | Thr | Leu | Pro | Tyr |
|---|---|---|---|---|---|---|---|---|---|---|---|---|---|---|---|
| | | 115 | | | | | 120 | | | | | 125 | | | |

| Thr | Gly | Asn | Tyr | Glu | Asn | Leu | Gln | Thr | Ala | Ala | His | Lys | Ile | Arg | Glu |
|---|---|---|---|---|---|---|---|---|---|---|---|---|---|---|---|
| | 130 | | | | | 135 | | | | | 140 | | | | |

| Asn | Ile | Asp | Leu | Gly | Leu | Pro | Ala | Leu | Ser | Ser | Ala | Ile | Thr | Thr | Leu |
|---|---|---|---|---|---|---|---|---|---|---|---|---|---|---|---|
| 145 | | | | | 150 | | | | | 155 | | | | | 160 |

| Phe | Tyr | Tyr | Asn | Ala | Gln | Ser | Ala | Pro | Ser | Ala | Leu | Leu | Tyr | Leu | Ile |
|---|---|---|---|---|---|---|---|---|---|---|---|---|---|---|---|
| | | | | 165 | | | | | 170 | | | | | 175 | |

| Gln | Thr | Thr | Ala | Glu | Ala | Ala | Arg | Phe | Lys | Tyr | Ile | Glu | Arg | His | Val |
|---|---|---|---|---|---|---|---|---|---|---|---|---|---|---|---|
| | | | 180 | | | | | 185 | | | | | 190 | | |

| Ala | Lys | Tyr | Val | Ala | Thr | Asn | Phe | Lys | Pro | Asn | Leu | Ala | Ile | Ile | Ser |
|---|---|---|---|---|---|---|---|---|---|---|---|---|---|---|---|
| | | 195 | | | | | 200 | | | | | 205 | | | |

| Leu | Glu | Asn | Gln | Trp | Ser | Ala | Leu | Ser | Lys | Gln | Ile | Phe | Leu | Ala | Gln |
|---|---|---|---|---|---|---|---|---|---|---|---|---|---|---|---|
| | 210 | | | | | 215 | | | | | 220 | | | | |

|     Asn<br>225 | Gln | Gly | Gly | Lys | Phe<br>230 | Arg | Asn | Pro | Val | Asp<br>235 | Leu | Ile | Lys | Pro | Thr<br>240 |

|     Gly | Glu | Arg | Phe | Gln<br>245 | Val | Thr | Asn | Val | Asp<br>250 | Ser | Asp | Val | Val | Lys<br>255 | Gly |

|     Asn | Ile | Lys | Leu<br>260 | Leu | Leu | Asn | Ser | Arg<br>265 | Ala | Ser | Thr | Ala | Asp<br>270 | Glu | Asn |

|     Phe | Ile | Thr<br>275 | Thr | Met | Thr | Leu | Leu<br>280 | Gly | Glu | Ser | Val | Val<br>285 | Asn |

( 2 ) INFORMATION FOR SEQ ID NO:14:

( i ) SEQUENCE CHARACTERISTICS:
        ( A ) LENGTH: 962 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bryonia dioica
        ( F ) TISSUE TYPE: leaf ( x i ) SEQUENCE DESCRIPTION: SEQ ID NO:14:

| GGGGGCCAAA | TTGGAAGGAA | AATAAATATG | AGATCGATTG | GGTTTTACTC | TGTTCTAGCT | 60 |
| CTGTATGTTG | GTGCTCATGT | TACAGAGGAC | GTTGATATCA | ACTTCTCTCT | AATAGGTGCG | 120 |
| ACTGGTGCAA | CCTACAAAAC | TTTTATAAGG | AATCTGCGCA | CCAAACTCAC | GGTTGGAACT | 180 |
| CCAAGGGTGT | ACGATATACC | TGTCCTGAGA | AACGCAGCAG | CCGGGCTCGC | GCGCTTTCAA | 240 |
| TTAGTTACCC | TCACAAATTA | CAATGGCGAA | TCTGTCACTG | TGGCTTTAGA | TGTAGTGAAC | 300 |
| GTGTACGTTG | TTGCATATCG | AGCTGGAAAC | ACTGCTTACT | TTCTCGCAGA | TGCATCAACA | 360 |
| GAAGCCAACA | ATGTGTTGTT | TGCAGGCATC | AATCATGTAA | GACTTCCTTA | TGGAGGGAAT | 420 |
| TACGATGGCC | TTGAGACAGC | TGCAGGCAGA | ATTTCGAGGG | AAAATATTGA | ACTTGGATTT | 480 |
| TCCGAAATAA | GTAGTGCCAT | TGGCAACATG | TTCCGCCACA | ACCCTGGTAC | GTCTGTCCCT | 540 |
| AGAGCATTTA | TTGTCATCAT | CCAAACAGTC | TCTGAGGCTG | CGAGATTTAA | ATATATCGAG | 600 |
| CAAAGAGTTT | CTGAAAATGT | TGGCACAAAG | TTTAAGCCAG | ACCCTGCGTT | TTTGAGCTTG | 660 |
| CAAAATGCTT | GGGGCAGTCT | CTCTGAACAA | ATACAAATCG | CACAAACTCG | CGGAGGGGAA | 720 |
| TTTGCTCGTC | CTGTCGAGCT | TCGAACTGTT | AGCAACACTC | CGACTTTTGT | GACCAATGTT | 780 |
| AATTCGCCTG | TTGTGAAAGG | CATTGCACTT | CTACTGTACT | TTAGAGTTAA | TGTTGGCACT | 840 |
| GATAATGTTT | TCGCAATGTC | CTTGTCAACC | TACTAGTACT | CATCAATCAA | ACTATACTGT | 900 |
| GTGCTTGTAT | GTGCAAGTAT | GGCAATAATA | AAGACTTAAT | CCTTTATGTT | AAAAAAAAAA | 960 |
| AA | | | | | | 962 |

( 2 ) INFORMATION FOR SEQ ID NO:15:

( i ) SEQUENCE CHARACTERISTICS:
        ( A ) LENGTH: 282 amino acids
        ( B ) TYPE: amino acid
        ( D ) TOPOLOGY: linear ( i i ) MOLECULE TYPE: protein ( v ) FRAGMENT TYPE: N-terminal ( v i ) ORIGINAL SOURCE:

(A) ORGANISM: Bryonia dioica
(F) TISSUE TYPE: leaf (xi) SEQUENCE DESCRIPTION: SEQ ID NO:15:

```
Met Arg Ser Ile Gly Phe Tyr Ser Val Leu Ala Leu Tyr Val Gly Ala
 1           5                  10                  15
His Val Thr Glu Asp Val Asp Ile Asn Phe Ser Leu Ile Gly Ala Thr
             20                  25                  30
Gly Ala Thr Tyr Lys Thr Phe Ile Arg Asn Leu Arg Thr Lys Leu Thr
             35                  40                  45
Val Gly Thr Pro Arg Val Tyr Asp Ile Pro Val Leu Arg Asn Ala Ala
     50                  55                  60
Ala Gly Leu Ala Arg Phe Gln Leu Val Thr Leu Thr Asn Tyr Asn Gly
 65              70                  75                  80
Glu Ser Val Thr Val Ala Leu Asp Val Val Asn Val Tyr Val Val Ala
                 85                  90                  95
Tyr Arg Ala Gly Asn Thr Ala Tyr Phe Leu Ala Asp Ala Ser Thr Glu
                100                 105                 110
Ala Asn Asn Val Leu Phe Ala Gly Ile Asn His Val Arg Leu Pro Tyr
             115                 120                 125
Gly Gly Asn Tyr Asp Gly Leu Glu Thr Ala Ala Gly Arg Ile Ser Arg
     130                 135                 140
Glu Asn Ile Glu Leu Gly Phe Ser Glu Ile Ser Ser Ala Ile Gly Asn
145                 150                 155                 160
Met Phe Arg His Asn Pro Gly Thr Ser Val Pro Arg Ala Phe Ile Val
                165                 170                 175
Ile Ile Gln Thr Val Ser Glu Ala Ala Arg Phe Lys Tyr Ile Glu Gln
                180                 185                 190
Arg Val Ser Glu Asn Val Gly Thr Lys Phe Lys Pro Asp Pro Ala Phe
             195                 200                 205
Leu Ser Leu Gln Asn Ala Trp Gly Ser Leu Ser Glu Gln Ile Gln Ile
     210                 215                 220
Ala Gln Thr Arg Gly Gly Glu Phe Ala Arg Pro Val Glu Leu Arg Thr
225                 230                 235                 240
Val Ser Asn Thr Pro Thr Phe Val Thr Asn Val Asn Ser Pro Val Val
                245                 250                 255
Lys Gly Ile Ala Leu Leu Leu Tyr Phe Arg Val Asn Val Gly Thr Asp
             260                 265                 270
Asn Val Phe Ala Met Ser Leu Ser Thr Tyr
             275                 280
```

(2) INFORMATION FOR SEQ ID NO:16:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

ACNTAYAARA CNTTYAT 17

(2) INFORMATION FOR SEQ ID NO:17:

(i) SEQUENCE CHARACTERISTICS:
(A) LENGTH: 20 base pairs
(B) TYPE: nucleic acid

```
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:
```

GGNGCNACNT ATAARACNAT                                                                    20

( 2 ) INFORMATION FOR SEQ ID NO:18:

```
    ( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:
```

CTCRATATAY TTRAAYCTCG CAGCCTC                                                            27

( 2 ) INFORMATION FOR SEQ ID NO:19:

```
    ( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:
```

GACTCGAGTC GACATCGATT TTTTTTTTT TTTTT                                                    35

( 2 ) INFORMATION FOR SEQ ID NO:20:

```
    ( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:
```

GACTCGAGTC GACATCG                                                                       17

( 2 ) INFORMATION FOR SEQ ID NO:21:

```
    ( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:
```

ACCACACTCA CGGTTGGAAC TCCA                                                               24

( 2 ) INFORMATION FOR SEQ ID NO:22:

```
    ( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA
```

( x i ) SEQUENCE DESCRIPTION: SEQ ID NO:22:

TGGAGTTCCA ACCGTGAGTG TGGT                                                                                    24

( 2 ) INFORMATION FOR SEQ ID NO:23:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:23:

CGTTCACTAC ATCTTAAGCC ACAGTGAC                                                                                28

( 2 ) INFORMATION FOR SEQ ID NO:24:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:24:

GACTTCCTTA TGGAGGGAAT TACGATGGCC TT                                                                           32

( 2 ) INFORMATION FOR SEQ ID NO:25:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:25:

GGCCACGCGT CGACTAGTAC GGGNNGGGNN GGGNNG                                                                       36

( 2 ) INFORMATION FOR SEQ ID NO:26:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:26:

CAGGAAACAG CTATGAC                                                                                            17

( 2 ) INFORMATION FOR SEQ ID NO:27:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:27:

CTGGCCGTCG TTTTAC                                                                                             16